(12) United States Patent
Sheng et al.

(10) Patent No.: US 12,257,456 B2
(45) Date of Patent: Mar. 25, 2025

(54) SYSTEMS AND METHODS FOR DYNAMIC CONTROL OF RADIATION DOSE IN RADIATION THERAPY

(71) Applicant: The Regents of the University of California, Oakland, CA (US)

(72) Inventors: Ke Sheng, Los Angeles, CA (US); Qihui Lyu, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 212 days.

(21) Appl. No.: 17/779,899

(22) PCT Filed: Nov. 25, 2020

(86) PCT No.: PCT/US2020/062392
§ 371 (c)(1),
(2) Date: May 25, 2022

(87) PCT Pub. No.: WO2021/108684
PCT Pub. Date: Jun. 3, 2021

(65) Prior Publication Data
US 2023/0015121 A1    Jan. 19, 2023

Related U.S. Application Data

(60) Provisional application No. 62/940,055, filed on Nov. 25, 2019.

(51) Int. Cl.
*A61N 5/10*    (2006.01)
(52) U.S. Cl.
CPC ......... *A61N 5/1067* (2013.01); *A61N 5/1036* (2013.01); *A61N 5/1045* (2013.01); *A61N 5/1081* (2013.01); *A61N 2005/1087* (2013.01)

(58) Field of Classification Search
CPC .. A61N 5/1036; A61N 5/1045; A61N 5/1067; A61N 5/1081; A61N 2005/1087
See application file for complete search history.

(56) References Cited

U.S. PATENT DOCUMENTS 5,631,943 A * 5/1997 Miles .................... A61B 6/548
378/102
6,240,161 B1    5/2001 Siochi
(Continued)

FOREIGN PATENT DOCUMENTS

WO    WO-2018183748 A1 * 10/2018   ........... A61B 5/0036
WO    2019048502 A1    3/2019

OTHER PUBLICATIONS

International Search Report issued for PCT/US2020/062392 dated Feb. 19, 2021.
(Continued)

*Primary Examiner* — Blake C Riddick
(74) *Attorney, Agent, or Firm* — Quarles & Brady LLP

(57) ABSTRACT

A system and method for delivering radiation therapy to a patient includes generating a radiation therapy plan and adjusting a shape of at least one of a plurality of multi-leaf collimators (MLCs) arranged in an arc about a patient bed to create a respective plurality of desired beam profiles for each of the plurality of MLCs to thereby implement the ultrafast radiation therapy plan delivery. The method further includes control a radiation therapy source to execute the radiation therapy plan by creating the respective plurality of desired beam profiles for each of the plurality of MLCs.

20 Claims, 9 Drawing Sheets

(56) References Cited

U.S. PATENT DOCUMENTS

| | | | |
|---|---|---|---|
| 6,907,105 B2 | 6/2005 | Otto | |
| 7,221,733 B1* | 5/2007 | Takai | A61N 5/1042 378/65 |
| 7,894,574 B1* | 2/2011 | Nord | A61N 5/1042 378/65 |
| 8,565,378 B2* | 10/2013 | Echner | A61N 5/1042 378/65 |
| 8,915,833 B1* | 12/2014 | Sahadevan | A61N 5/1084 600/1 |
| 2003/0202632 A1* | 10/2003 | Svatos | A61N 5/1042 378/65 |
| 2004/0179648 A1* | 9/2004 | Svatos | A61N 5/103 378/65 |
| 2005/0008121 A1* | 1/2005 | Low | A61N 5/1027 378/65 |
| 2006/0045238 A1* | 3/2006 | Nguyen | A61N 5/103 378/65 |
| 2007/0086569 A1* | 4/2007 | Johnsen | A61N 5/1045 378/65 |
| 2008/0123813 A1* | 5/2008 | Maurer | A61N 5/1042 378/96 |
| 2008/0144772 A1* | 6/2008 | Yi | A61N 5/1049 378/65 |
| 2009/0001296 A1* | 1/2009 | Kuduvalli | A61N 5/1042 250/505.1 |
| 2009/0041188 A1* | 2/2009 | Keall | A61N 5/1042 378/65 |
| 2009/0074148 A1* | 3/2009 | Echner | G21K 1/04 378/152 |
| 2009/0220046 A1* | 9/2009 | Ji | A61N 5/1042 378/65 |
| 2010/0016649 A1* | 1/2010 | Prionas | A61N 5/1081 600/1 |
| 2010/0020932 A1* | 1/2010 | Yi | A61N 5/1049 378/65 |
| 2010/0054408 A1* | 3/2010 | Echner | A61N 5/1042 378/65 |
| 2010/0252754 A1* | 10/2010 | Brown | A61N 5/1042 250/492.1 |
| 2012/0004518 A1* | 1/2012 | D'Souza | A61B 5/704 600/301 |
| 2012/0043481 A1* | 2/2012 | Mansfield | A61N 5/1045 250/492.1 |
| 2012/0256103 A1* | 10/2012 | Luzzara | G21K 1/046 250/492.1 |
| 2013/0000428 A1* | 1/2013 | Ji | A61N 5/1045 74/30 |
| 2013/0165770 A1* | 6/2013 | Li | A61N 5/1067 600/430 |
| 2013/0216026 A1* | 8/2013 | Nord | G21K 1/02 378/65 |
| 2014/0107390 A1* | 4/2014 | Brown | A61N 5/1045 703/11 |
| 2014/0275704 A1* | 9/2014 | Zhang | A61N 5/1067 600/1 |
| 2014/0275963 A1* | 9/2014 | Shvartsman | A61N 5/1049 600/411 |
| 2015/0231413 A1* | 8/2015 | Grady | A61N 5/1082 378/65 |
| 2016/0071623 A1* | 3/2016 | Schewiola | A61N 5/1045 378/152 |
| 2016/0310763 A1* | 10/2016 | Grady | A61B 6/06 |
| 2017/0028221 A1* | 2/2017 | Kontaxis | A61N 5/1038 |
| 2017/0050051 A1* | 2/2017 | Berbeci | A61N 5/1064 |
| 2017/0148536 A1* | 5/2017 | Kawrykow | A61N 5/1045 |
| 2017/0189716 A1* | 7/2017 | Wang | A61N 5/1045 |
| 2018/0028839 A1* | 2/2018 | Yoshimizu | A61N 5/1065 |
| 2018/0161602 A1* | 6/2018 | Kawrykow | A61B 6/0407 |
| 2018/0200540 A1* | 7/2018 | Flynn | A61N 5/1001 |
| 2018/0311509 A1* | 11/2018 | Sjölund | A61N 5/1031 |
| 2018/0345042 A1* | 12/2018 | Voronenko | A61N 5/1039 |
| 2020/0016432 A1* | 1/2020 | Maolinbay | A61N 5/1067 |
| 2020/0038685 A1* | 2/2020 | Kundapur | G21K 1/025 |
| 2020/0234443 A1* | 7/2020 | Yan | G06T 7/248 |
| 2021/0038916 A1* | 2/2021 | Nguyen | A61N 5/1067 |
| 2021/0038921 A1* | 2/2021 | Nguyen | A61B 6/032 |
| 2021/0166801 A1* | 6/2021 | Seeber | G05B 19/05 |
| 2021/0187322 A1* | 6/2021 | Zhong | G21K 1/046 |
| 2021/0220671 A1* | 7/2021 | Eriksson | A61N 5/1037 |
| 2021/0339047 A1* | 11/2021 | Janardhanan | A61N 5/1031 |
| 2022/0126117 A1* | 4/2022 | Voronenko | A61N 5/1043 |

OTHER PUBLICATIONS

International Preliminary Report on Patentability issued for PCT/US2020/062392 issued May 17, 2022.

* cited by examiner

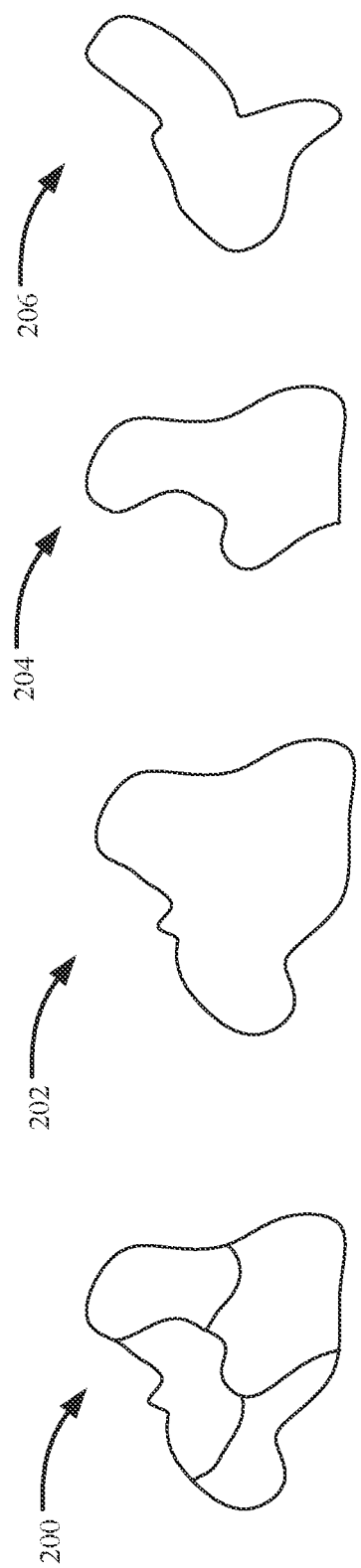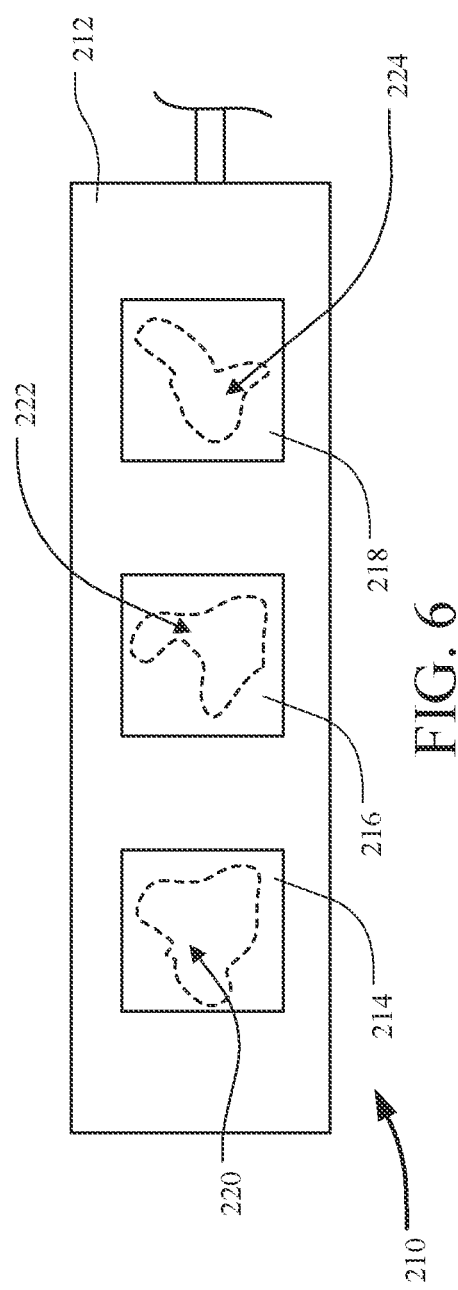

SYSTEMS AND METHODS FOR DYNAMIC CONTROL OF RADIATION DOSE IN RADIATION THERAPY

CROSS-REFERENCE TO RELATED APPLICATIONS

This application represents the national stage entry of PCT/US2020/062392 filed on Nov. 25, 2020 and claims priority to U.S. Patent Application No. 62/940,055 filed Nov. 25, 2019, and entitled, "Systems and methods for dynamic control of x-ray dose in radiation therapy," which is hereby incorporated by reference in its entirety.

STATEMENT REGARDING FEDERALLY SPONSORED RESEARCH

This invention was made with government support under CA255432 awarded by the National Institutes of Health. The government has certain rights in the invention.

BACKGROUND

Radiation therapy ("RT") has gone through a series of technological revolutions in the last few decades. With intensity modulated RT ("IMRT"), it became possible to produce highly conformal dose distributions, whereby the bulk radiation dose is delivered within the extent of a tumor. More recently, short, high-dose, therapy techniques, often referred to as "FLASH" methods, have been theorized as effective for a variety of clinical indications. In theory, ultra-high-dose radiation therapy that is delivered over a very-short duration may be more biologically effective than conventional radiotherapy. As a general example, the FLASH dose rate is 100 times or greater than the conventional radiotherapy.

There are a few proposed modalities that some have attempted to use to perform a FLASH method. First, electrons-based therapy systems may be used. These electron based systems use high-energy electrons to impinge on a target to produce x-rays. The conversion efficiency is extremely low. If the target is moved, electron dose rate is 100 times higher than the corresponding X-ray dose rate. However, the electrons from existing medical linear accelerators only have shallow penetration, which is unsuited to treat deep tumors.

Second, some have tried to use proton therapy systems to perform FLASH methods. Select proton systems can produce extremely high scanning beam dose rates in tissues. They are therefore potentially capable of performing the FLASH method. The challenge is that the energy switch of Bragg Peaks from one depth to another takes a few seconds, making volume dose delivery using Bragg Peaks too slow for FLASH methods. Alternatively, protons can be used to perform FLASH methods using the entrance tail of the dose in the transmissive mode. This limits both the depth of treatment and the quality of dose distribution, which is not only worse than the typical proton treatment but also worse than the state of the art x-ray dose.

The third modality is often referred to as "PHASER." PHASER systems use a circular array of linear accelerators powered by a high-power Klystron with phase array waveguide. The energized electrons are magnetically steered to impinge on a honeycomb-shaped target/intensity modular array for IMRT. This method may in theory generate and deliver highly conformal high dose rate therapy plans but whether if the dose rate can be high enough for FLASH is questionable due to the low X-ray conversion efficiency using the proposed target. PHASER will not be available in the near future and is risky due to its dependence on the development of several new technologies.

As indicated above, implementing FLASH is conventionally difficult. Thus, there is a need to overcome the practical and clinical limitations that stop FLASH or other high-dose rate, short-duration, therapy processes from being clinically available.

SUMMARY OF THE DISCLOSURE

The present disclosure provides systems and methods that facilitates clinical implementation of high-dose rate, short duration radiation therapy plans. Compared with previous attempts, the disclosed systems, apparatus, and methods achieve both state-of-the-art dose rate and high-quality dose distribution. In particular, a multi-collimator system is provided that provides the adaptable dose control and can meet the speed requirements for ultra-high dose plans, such as implementing FLASH protocols.

Some non-limiting examples of the disclosure provide systems and methods for delivering high-dose radiotherapy to a tumor, while controlling the impact on normal tissue. In one configuration, a radiation source is provided to deliver a high dose of radiation at a high speed. There a plurality or array of multi-leaf collimators (MLCs) that are arranged between the radiation source and a patient bed and, thereby, the patient. The MLCs shape the radiation beam produced by the radiation source. By having a plurality of MLCs, the MLCs can be pre-positioned and pre-configured to create the desired shape for each beam path in a radiation therapy plan. That is, by having a dedicated MLC for each radiation beam path (e.g., as defined in a patient specific radiation treatment plan), it is not necessary to adjust an MLC for each new position of the radiation source and beam path. Thus, the present disclosure breaks from the traditional paradigm of coupling one or more MLCs with the radiation source, to move with the radiation source, and necessitate adjustment/reconfiguration of the MLC as the radiation source moves to each new position to deliver along an associated new beam path. Instead, the radiation source can move to each new position where an MLC is already located and may be pre-adjusted or pre-configured to shape the beam in a manner desired for the beam path associated with the MLC according to the radiation therapy plan.

In some configurations, a ring where the plurality or array of MLCs are mounted can be static or rotate during the treatment process. The plurality of MLCs may form an arc or ring. When the radiation source is aligned with a particular MLC, the radiation source is triggered to produce a very-high dose along the beam path associated with that particular MLC. Each MLC can be pre-adjusted or pre-configured into a shape providing a desired aperture for the beam path before the start of treatment and/or before arrival of the radiation source at the MLC. Thus, high-speed radiation therapy plans can be implemented, such as FLASH therapy plans, without the need to engineer a single MLC that is capable of the mechanical movements needed to adjust the beam shape at each new position of the radiation therapy source. A volumetric modulated arc optimization method can be used to optimize the aperture shapes. A new group of MLC shapes can be formed between two treatments based on a treatment plan. The treatment plan can be accomplished with FLASH dose rate and high-quality dose distribution.

Some aspects of the disclosure provide a radiation therapy system. The radiation therapy system can include a radiation source configured to emit a radiation therapy beam toward a patient having a tumor to effectuate a radiation therapy process, and a plurality of dynamically-adjustable collimators, each of the dynamically-adjustable collimators configured to be independently controlled to create a respective attenuation profile at each of the dynamically-adjustable collimators. The radiation therapy system can include a controller device that can be configured to adjust the respective attenuation profile at each of the dynamically-adjustable collimators based on a shape of the tumor relative to a respective beam path defined by a path followed from the radiation source through a respective dynamically-adjustable collimator and to the tumor of the patient. The controller device can be configured to, to effectuate the radiation therapy process, control at least one of a position of the radiation or the plurality of dynamically-adjustable collimators relative to the patient to deliver the radiation therapy beam through each of the plurality of dynamically-adjustable collimators to match a shape of the radiation therapy beam to the shape of the tumor relative to the respective beam path defined by the path followed from the radiation source through a respective dynamically-adjustable collimator and to the tumor of the patient.

In some non-limiting examples, only one of the dynamically-adjustable collimators are used at a time to attenuate the radiation beam according to their respective attenuation profiles.

In some non-limiting examples, a first dynamically-adjustable collimator that is part of the plurality of the dynamically-adjustable collimators is moved out of alignment with the radiation beam that is stationary. In some non-limiting examples, a second the dynamically-adjustable collimator that is part of the plurality of the dynamically-adjustable collimators is moved into alignment with the radiation beam that stationary.

In some non-limiting examples, the radiation source is configured to move out of alignment with a first dynamically-adjustable collimator and into alignment with a second dynamically-adjustable collimator while the first and second dynamically-adjustable collimators are stationary, the first and second dynamically-adjustable collimators being part of the plurality of dynamically-adjustable collimators.

In some non-limiting examples, each radiation attenuation profile of each dynamically-adjustable collimator is different. In some non-limiting examples, each radiation attenuation profile of each dynamically-adjustable collimator is based on a two-dimensional projection of a three-dimensional representation of a tumor of the patient at different orientations about the patient.

In some non-limiting examples, each dynamically-adjustable collimator is a multi-leaf collimator (MLC) having a plurality of indecently controllable leaves.

In some non-limiting examples, the controller device is configured to adjust the positions of the independently controllably leaves that define the respective radiation attenuation profile for each MLC, based on a radiation treatment plan for the patient.

In some non-limiting examples, the controller device is configured to adjust the respective radiation attenuation profile for each dynamically-adjustable collimator, prior to the radiation therapy system beginning the radiation treatment for the patient.

In some non-limiting examples, the attenuation profile for each dynamically-adjustable collimator is not adjusted during the entire duration of the radiation treatment for the patient.

In some non-limiting examples, the radiation therapy system can include a table configured to support the patient. In some non-limiting examples, the plurality of dynamically-adjustable collimators are oriented concentrically about the table.

In some non-limiting examples, each of the dynamically-adjustable collimators are located at a different concentric position about the table. In some non-limiting examples, each pair of adjacent MLCs defines a concentric arc therebetween. In some non-limiting examples, the sum of the concentric arcs spans a concentric arc length about the patient. In some non-limiting examples, the concentric arc length is 360 degrees.

In some non-limiting examples, the radiation therapy system can include a robotic arm having a number of articulable joints. The robotic arm can be in communication with an controllable by the controller device. The radiation therapy system can include a housing that secures and couples together the plurality of dynamically-adjustable collimators. The housing can be coupled to the robot arm. In some non-limiting examples, the controller device is configured to adjust the positioning of the robotic arm relative to the radiation source, thereby selectively aligning a given dynamically-adjustable collimator with the radiation beam.

In some non-limiting examples, each of the dynamically-adjustable collimators are concentrically oriented relative to a plane that is substantially perpendicular, or substantially parallel to the radiation therapy beam.

In some non-limiting examples, each pair of adjacent dynamically-adjustable collimators defines a concentric arc therebetween, and the sum of the concentric arcs spans a concentric arc length about an axial axis that is perpendicular to the plane. In some non-limiting examples, the concentric arc length is 360 degrees.

In some non-limiting examples, the housing is rotatable about the axial axis so that with the robotic arm stationary, the housing rotates to bring one of the dynamically-adjustable collimators within the plurality of dynamically-adjustable collimators into alignment with the radiation therapy beam.

In some non-limiting examples, the computing device is configured to cause a motor to rotate the housing about the axial axis.

In some non-limiting examples, the plurality of dynamically-adjustable collimators are aligned along an axis.

In some non-limiting examples, one of the plurality of dynamically-adjustable collimators is a bowtie filter having at least two independently moveable leaves.

In some non-limiting examples, a first dynamically-adjustable collimator includes a plurality of independently controllable leaves. In some non-limiting examples, the collective positioning of the plurality of independently controllable defines a void of the first dynamically-adjustable collimator, which defines the attenuation profile of the first dynamically-adjustable collimator.

In some non-limiting examples, the controller device is configured to adjust the collective positioning of the independently controllable leaves of a first dynamically-adjustable collimator between a first position that defines the void to a second position where the void is eliminated at a duty cycle. In some non-limiting examples, the first position defines an on portion of the duty cycle and the second position defines an off portion of the duty cycle.

In some non-limiting examples, the duty cycle is based on a thickness of the tumor along the path followed from the radiation source through the first dynamically-adjustable collimator and through the tumor. In some non-limiting examples, the path follows a three dimensional line.

In some non-limiting examples, the radiation therapy beam has an ultra-high dose and lasts for a short duration. In some non-limiting examples, the ultra-high dose can beg at least 100 Gy/s. In some non-limiting examples, the short duration can be between 0.01 seconds and 0.5 seconds.

In some non-limiting examples, the radiation therapy beam is an X-ray beam.

Some aspects of the disclosure provide a computer-implemented method for providing radiation treatment for a patient. The method can include receiving, using one or more computing devices, a radiation treatment plan for the patient, adjusting for a plurality of adjustable collimators, using the one or more computing devices, each attenuation profile of each adjustable collimator based on the radiation treatment plan, and moving, using the one or more computing devices, at least one of a radiation source, or a first adjustable collimator so that the radiation source aligns with a first radiation beam path according to the radiation treatment plan, and the first adjustable collimator corresponding to the first radiation beam path is aligned with the first radiation beam path, the attenuation profile of the first adjustable collimator having been adjusted according to the first radiation beam path. The method can include causing, using the one or more computing devices, the radiation source to emit a first radiation beam along the first radiation beam path and through the first adjustable collimator so that the first radiation beam is attenuated according to the attenuation profile of the first adjustable collimator before being delivered to a tumor of the patient.

In some non-limiting examples, the first adjustable collimator is moved by at least one of rotating, using the one or more computing devices, the first adjustable collimator relative to the radiation source to align the first adjustable collimator with the first radiation beam path, or translating, using the one or more computing devices, the first adjustable collimator relative to the radiation source to align the first adjustable collimator with the first radiation beam path.

In some non-limiting examples, the method can include moving, using the one or more computing devices, the radiation source in a position that aligns with the first radiation beam path of the radiation treatment plan.

In some non-limiting examples, the method can include moving, using the one or more computing devices, the radiation source until the radiation source aligns with the first radiation beam path of the radiation treatment plan and the first adjustable collimator, with the first adjustable collimator stationary.

In some non-limiting examples, the radiation treatment plan defines a plurality of radiation beam paths that includes the first radiation beam path. The method can include assigning, using the one or more computing devices, each adjustable collimator to a different radiation beam path of the plurality of radiation beam paths, and adjusting, using the one or more computing devices, each attenuation profile of each adjustable collimator based on its corresponding radiation beam path.

In some non-limiting examples, each attenuation profile of each adjustable collimator corresponds to a shape of a tumor that is defined by the corresponding radiation beam path. In some non-limiting examples, each corresponding radiation beam path follows a path that extends from the radiation source and to the patient.

In some non-limiting examples, the method can include after emitting the first radiation beam for a period of time, stopping, using the one of the computing devices, the radiation source from emitting the first radiation beam. In some non-limiting examples, the method can include when the radiation source has stopped emitting the first radiation beam, moving, using the one or more computing devices, the at least one of the radiation source, or the first adjustable collimator out of alignment with the first radiation beam path. In some non-limiting examples, the method can include moving, using the one or more computing devices, at least one of a second adjustable collimator or the radiation source so that the radiation source aligns with a second radiation beam path according to the radiation treatment plan, and the second adjustable collimator that corresponds with the second radiation beam path is aligned with the second radiation beam path.

In some non-limiting examples, the attenuation profiles of the first and second adjustable collimators are different.

In some non-limiting examples, the first adjustable collimator and the second adjustable collimator are multi-leaf collimators (MLCs). In some non-limiting examples, at least one of a size or a shape of a void of the first adjustable collimator at least partially defines its attenuation profile. In some non-limiting examples, at least one of a size or a shape of a void of the second adjustable collimator at least partially defines its attenuation profile.

In some non-limiting examples, the method can include after adjusting, using the one or more computing devices, each attenuation profile of each adjustable collimator based on the radiation treatment plan, further adjusting an attenuation profile of one of the adjustable collimators.

In some non-limiting examples, the further adjustment of the attenuation profile of the one of the adjustable collimators can occur at least one of after the first radiation beam has been emitted for a duration defined by the radiation treatment plan, or during emission of the first radiation beam during the duration defined by the radiation treatment plan.

In some non-limiting examples, the method can include moving, using the one or more computing devices, a collimator assembly having a first collimator with a first attenuation profile and a second collimator with a second attenuation profile, between two positions according to a duty cycle. In some non-limiting examples, the first position occurs when the first collimator is aligned with the radiation source so that a given radiation beam passing through the first collimator is attenuated according to the first attenuation profile of the first collimator. The first position can correspond to an off position of the duty cycle. In some non-limiting examples, the second position occurs when the second collimator is aligned with the radiation source so that the given radiation beam passing through the second collimator is attenuated according to the second attenuation profile of the second collimator. The second position can correspond to an on position of the duty cycle. In some non-limiting examples, in the second position, the given radiation beam is not attenuated by the first collimator. In some non-limiting examples, the second attenuation profile attenuates a radiation beam less than the first attenuation profile.

In some non-limiting examples, the one or more computing devices move the collimator assembly according to the duty cycle while the radiation source emits the first radiation beam.

In some non-limiting examples, the duty cycle is based on a thickness of a tumor along the first radiation beam path.

In some non-limiting examples, the first radiation beam is emitted for a duration, the duration being between 0.01 seconds and 0.5 seconds. The first radiation beam can be an X-ray beam.

In some non-limiting examples, the one or more computing devices adjusts each attenuation profile of each adjustable collimator prior to causing the radiation source to emit the first radiation beam.

In some non-limiting examples, after adjusting the attenuation profile of each adjustable collimator, the attenuation profile of each adjustable collimator is not adjusted during the extent of radiation treatment according to the radiation treatment plan.

Some aspects of the disclosure provide a radiation therapy system. The radiation therapy system can include a radiation therapy source configured to deliver a radiation therapy beam toward a patient bed, a gantry configured to receive a patient bed to arrange the gantry between the radiation therapy source and the patient bed, and a plurality of multi-leaf collimators (MLCs) positioned about the gantry, between the radiation therapy source and the patient bed, to define a respective beam path for each of the MLCs. The radiation therapy system can include a controller configured to adjust a configuration of each of the MLCs to shape the radiation therapy beam passing through a respective one of the MLCs to a shape specific to the beam path when the radiation therapy source is aligned with the respective one of the MLCs.

In some non-limiting examples, the plurality of MLCs are arranged about the gantry to form a ring between the patient bed and the radiation therapy source.

In some non-limiting examples, the controller is configured to change an orientation of each of the plurality of MLCs when the radiation therapy source is not arranged to deliver the radiation therapy beam along the beam path associated with a given MLC in the plurality of MLCs.

In some non-limiting examples, the controller is configured to control a position of the radiation therapy source to traverse about the gantry.

In some non-limiting examples, the MLCs form an arc about the gantry.

In some non-limiting examples, the controller is further configured to adjust the configuration of each of the plurality of MLCs based on a target size and a desired radiation beam shape for a particular position relative to the patient bed.

In some non-limiting examples, the plurality of MLCs form an arc about the patient bed.

In some non-limiting examples, the controller is configured to dynamically adjust the array of MLCs and the radiation therapy source based on at least one of beam path, dose, intensity of radiation therapy beam, and shape of the array of the MLCs during execution of a radiation therapy plan.

In some non-limiting examples, the controller is configured to cause the radiation therapy source to rotate in a first direction about the patient bed and cause the plurality of MLCs to rotate in a second direction, opposite to the first direction, about the patient bed.

Some aspects of the disclosure provide a method for delivering radiation therapy to a patient. The method can include generating a radiation therapy plan, adjusting a shape of at least one of a plurality of multi-leaf collimators (MLCs) arranged in an arc about a patient bed to create a respective plurality of desired beam profiles for each of the plurality of MLCs to thereby implement the radiation therapy plan, and controlling a radiation therapy source to execute the radiation therapy plan by creating the respective plurality of desired beam profiles for each of the plurality of MLCs.

In some non-limiting examples, step (b) can further include adjusting the shape based on at least one a dosage for radiation therapy or a time for receiving the dose for radiation therapy.

In some non-limiting examples, the method can include moving the radiation therapy source in a first direction about the target region and moving the plurality of MLCs in a second direction about the target region. In some non-limiting examples, the first and second directions are opposite.

In some non-limiting examples, the method can include independently adjusting a shape of each of the plurality of MLCs.

Some aspects of the disclosure provide a radiation therapy system. The radiation therapy system can include a radiation source configured to emit a radiation therapy beam along a beam path towards a patient, a collimator positioned in the beam path to present a first radiation attenuation profile to the radiation therapy beam to attenuate the radiation therapy beam prior to reaching the patient, and a first multi-leaf collimator (MLC) having a plurality of independently controllable leaves, the positions of the plurality of independently controllable leaves defining a second radiation attenuation profile, the first attenuated radiation therapy beam being provided to the first MLC to attenuate the first attenuated radiation therapy beam according to the second radiation attenuation profile, the second attenuated radiation therapy beam being delivered to the patient.

In some non-limiting examples, the collimator is at least one of a flattening filter for the radiation therapy beam, or an MLC.

In some non-limiting examples, the collimator is positioned in front of the radiation source.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the disclosure.

BRIEF DESCRIPTION OF THE DRAWINGS

The following drawings are provided to help illustrate various features of example non-limiting examples of the disclosure, and are not intended to limit the scope of the disclosure or exclude alternative implementations.

FIG. 5 shows a schematic illustration of a 3D volume of a tumor of a patient, and three different two-dimensional ("2D") projections of the 3D volume of the tumor.

FIG. 6 shows a schematic illustration of an example of a collimator assembly.

DETAILED DESCRIPTION OF THE PRESENT DISCLOSURE

Figure 1:
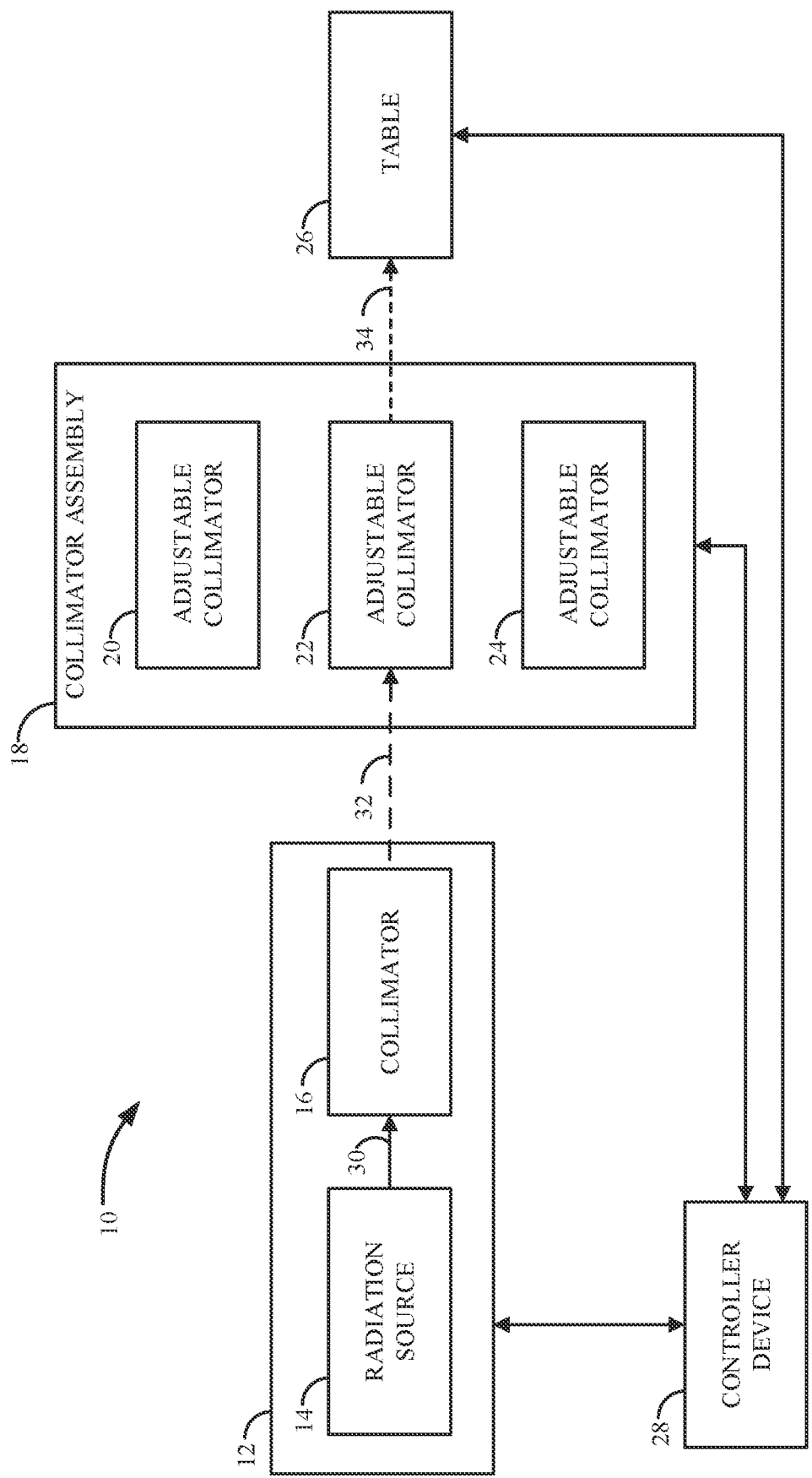
FIG. 1 shows a schematic block diagram of a radiation therapy system.

As described above, particle based FLASH techniques that utilize particles to bombard a treatment site, such as a tumor, have disadvantages that currently make these systems largely impractical. For example, electron based systems require expensive and bulky linear accelerators necessary for accelerating the bombarding electrons to a particular speed (e.g., the speed necessary for producing at least 100 Gy/s or a greater dose rate). Thus, the high cost of these electron based systems (and other reasons) prevent their widespread adoption. Some alternative approaches to particle based FLASH techniques have theorized using X-rays to implement the FLASH technique. However, these X-ray based FLASH techniques have their own problems. For example, proper modulation of these X-rays beams (e.g., those being of a sufficient speed and energy does) is difficult when using conventional approaches, such as a conventional multi-leaf collimator ("MLC").

While MLCs have a large number of leaves (e.g., thin tungsten leaves) that can be manipulated to adjust the shape of the radiation field, which in this case is an X-ray radiation field, the leaves of the MLC must be collectively moved— often requiring moving many of the individual leaves a large distance. Because the maximum speed of adjusting a given leaf of the MLCs is quite slow (e.g., a maximum speed of 2.5 cm/s to 5 cm/s), the MLCs cannot be adjusted in the appropriate time. In fact, for proper implementation of the FLASH technique with X-rays, the individual leaves of the MLC would need to move 100 times faster, which is currently mechanically impossible without significantly sacrificing accuracy and stability–tradeoffs that are not a clinically-viable.

The relatively slow speed of the MLC leaves causes problems for the implementation of X-ray based FLASH techniques, but also causes issues with more traditional x-ray radiation therapy approaches. In general, radiation treatment speed and radiation treatment accuracy are at least two important aspects for improved patient outcome, both for the individual patient and the patient population as a whole (e.g., those that could benefit from radiation therapy at the particular location). For example, regarding radiation treatment speed, slower radiation treatment speeds can cause longer radiation treatment times for the patient. This can cause issues with individual treatments, such as, increased risk that the patient undesirably moves during the treatment session (e.g., as undesirable movement increases with increasing treatment times because patients can become impatient, lose focus, become uncomfortable, etc.), and decreased patient compliance to the entire radiation treatment plan (e.g., patients avoiding radiation treatment sessions due to the lengthy time), etc. In some cases, this undesirable movement can cause healthy regions of the subject to be irradiated. Thus, to prevent treatment times from becoming exceedingly long, practitioners may decide to deviate from a radiation treatment plan that is specifically tailored to the patient. For example, the modified radiation treatment plan may not irradiate every beam path that was previously determined (e.g., by decreasing the number of different predetermined radiation beam paths). As such, this deviation can then decrease the accuracy of the radiation treatment for the individual.

Regarding the patient population that could benefit from radiation treatment at a particular radiation facility, is undesirably impacted by longer treatment times. For example, increased individual radiation treatment times may cause a bottleneck for this patient population. In other words, some patients may not be able to be seen (altogether) or at the appropriate times that is determined by their entire radiation treatment regimen. For example, at least due to increased individual radiation treatment times, some patients that require multiple sessions, cannot be efficiently scheduled when compared to their treatment regimen.

Some non-limiting examples of the disclosure address these issues (and others) by providing systems and methods for dynamic control of radiation doses and profiles. For example, some non-limiting examples of the disclosure provide a radiation therapy system that includes a plurality of adjustable collimators, each of which can be placed into alignment with a radiation beam (e.g., by moving the radiation source or the adjustable collimators). Each of the plurality of adjustable collimators can define and adjust its radiation attenuation profile, which can correspond to a particular orientation (and position) of a particular radiation beam relative to the subject, as defined by a patient specific radiation treatment plan (e.g., a radiation treatment plan that is tailored to a particular patient). In this way, each of the plurality of adjustable collimators can be quickly moved into (or out of) alignment with the radiation beam, which can be much faster than the speed of moving individual leaves of an adjustable collimator (e.g., a multi-leaf collimator). Thus, this configuration can both increase the speed and accuracy of individual radiation treatments.

In some configurations, the respective attenuation profile of each of the plurality of adjustable collimators can be adjusted to a desired state (e.g., to match a radiation treatment plan) prior to providing any radiation to a patient (e.g., before the start of a radiation treatment session). In fact, the respective attenuation profiles can be adjusted during previously unutilized downtime, such as during moving a patient, during patient charting, during configuring a patient on a table, etc., thereby increasing the time efficiency for a given radiation treatment system. In some cases, the respective attenuation profile for some of the plurality of adjustable collimators can be adjusted during the radiation treatment. For example, as a radiation beam emits through a given adjustable collimator, one (or more) of the other adjustable collimators can be adjusted while the attenuated radiation beam is provided to the patent. In this way, the unused time during treatment while particular adjustable collimators are not being used can be utilized. As another example, some of the attenuation profiles of the plurality of adjustable collimators can be adjusted, based on a previously performed treatment deviating from the patient tailored radiation treatment plan. In particular, suppose a patient moved slightly during treatment of one radiation beam thereby missing a portion of the tumor at that particular beam orientation. In this case, the radiation treatment plan can be modified to adjust the previously determined (and implemented) radiation attenuation profiles of the other adjustable collimators that have yet to be used. Thus, when the other adjustable collimator(s) have been used, the previously missed radiation dose at that particular angle can be compensated by using the newly adjusted adjustable collimators.

In some non-limiting examples, because the time needed to adjust a given adjustable collimator is largely made obsolete by having a plurality of additional (preset) collimators (e.g., corresponding to a patient specific radiation treatment plan), the adjustable collimators themselves can be made of a far higher resolution. For example, when the adjustable collimators are implemented as multi-leaf collimators (MLCs), each of these MLCs can have a greater number of leaves, and correspondingly having smaller thicknesses. In this way, the attenuation profile of a given MLC can be more complex, leading to a more accurate radiation treatment dosage scheme for the patient. In some non-limiting examples, some or each of the adjustable collimators can have 60 or more independently controllable leaves, where each independently controllable leaf can have a thickness of 5 mm or less.

FIG. 1 shows a schematic block diagram of a radiation therapy system 10. The radiation therapy system can include a gantry 12 having a radiation source 14 and a collimator 16, a collimator assembly 18 that includes adjustable collimators 20, 22, 24, a table 26, and a controller device 28. The gantry 12 generally supports and secures the radiation source 14, and the collimator 16. For example, the gantry 12 can be positioned relative to the table 26 that supports a patient, and can rotate about an axial axis (e.g., that intersects with the table 26) to move the radiation source 14 and the collimator 16 together about the axial axis. In some cases, the gantry 12 can be a cylinder gantry, a ring gantry, a C-arm gantry, etc. In other configurations, the gantry 12 can be implemented in other ways. For example, the gantry 12 can be coupled to a robot arm (e.g., an end effector of a robot arm), which can selectively move the gantry 12 and thus the radiation source 14 and collimator 16 to different locations about the table 26. Thus, the radiation source 14 can emit radiation beams that follow various paths having different orientations relative to the patient.

In some non-limiting examples, the radiation source 14 can be an X-ray beam forming assembly configured to emit X-rays, or in other cases, the radiation source 14 can be a linear accelerator ("LINAC") or other particle accelerator configured to accelerate particles (e.g., electrons, protons, etc.), such as, a cyclotron (e.g., a synchrotron). In some non-limiting examples, the collimator 16 can be a flattening filter, a MLC, a bowtie filter, etc. In some configurations, the collimator 16 can be removed. As shown, the controller device 28 is in communication with the gantry 12 and is in communication with the radiation source 14. Thus, the controller device 28 can cause the radiation source to adjust how a radiation beam is emitted from the radiation source (e.g., by turning the radiation source on and off, or adjusting the intensity of the radiation beam). The controller device 28 can also cause the gantry 12 to move, such as by rotating the gantry 12 about an axial axis, or by causing a robotic arm coupled to the gantry 12 to move. In some configurations, such as when the collimator 16 is implemented as a MLC, the controller device can adjust an attenuation profile of the collimator 16 thereby adjusting how the radiation beam emitted by the radiation source 14 is attenuated (e.g., as the radiation beam passes through the collimator 16).

As shown, the collimator assembly 18 includes the adjustable collimators 20, 22, 24 that each can adjust their attenuation profile (e.g., how the radiation beam is attenuated as it passes through a given adjustable collimator). For example, the adjustable collimators 20, 22, 24 can each include a plurality of independently adjustable leaves, that can be collectively moved to define (and change) their respective attenuation profile. In some configurations, these independently controllable leaves can be formed out of materials that absorb significant amounts of radiation, such as lead, tungsten, etc. The individually controllable leaves can be mechanically moved (e.g., translated) by respective a motor. Thus, the collective position of the independently controllable leaves can be adjusted by causing some (or all) of the motors to translate their respective independently controllable leaf. As shown, the controller device 28 is in communication with the collimator assembly 18, and each of the adjustable collimators 20, 22, 24. Thus, the controller device 28 can adjust the attenuation profile of each adjustable collimator 20, 22, 24 (e.g., by moving some or all of the independently controllable leaves via the respective motors).

In some non-limiting examples, the collimator assembly 18 can move relative to the gantry 12. For example, the collimator assembly 18 can be coaxially positioned around the table 26 so that the adjustable collimators 20, 22, 24 are (concentrically) positioned around the table 26. In this case, for example, a motor can cause the collimators 20, 22, 24 to rotate in a first directional rotation around the axial axis that interests the table 26, and in a second rotational direction around the axial axis. In this way, one of the adjustable collimators 20, 22, 24 at a time can be brought into alignment with the radiation beam emitted by the radiation source 14 (and attenuated by the collimator 16). In other non-limiting examples, the collimator assembly 18 can be mounted on a robot arm (e.g., similarly to the configuration of the robot arm of the gantry 12 above). For example, the collimator assembly 18 can be mounted on a robot arm (e.g., on or defining the end effector of the robot arm) that is in communication with the controller device 28. In this way, the controller device 28 can cause the robot arm to move the collimator assembly 18 so that one of the adjustable collimators 20, 22, 24 is brought into alignment with the radiation beam emitted by the radiation source 14. In some cases, the robot arm that has the collimator assembly 18 coupled thereto can have its base coupled to the gantry 12. In this way, the robot arm with the collimator assembly 18 can rotate along with gantry 12, as appropriate. This can simplify the coordinate systems between the robot arm and the gantry 12, at least because the position of the robot arm can be more easily related to the position of the gantry 12.

In some cases, the collimator assembly 18 can include a support arm and a housing coupled to the support arm that supports the adjustable collimators 20, 22, 24. In this case, the support arm can be coupled to the gantry 12 so that the upper surfaces of the adjustable collimators 20, 22, 24 (and a surface of the housing), are substantially parallel (e.g., deviating from parallel by less than 10%) to the axial axis defined by the table 26. The collimators 20, 22, 24 can be concentrically positioned about the housing (e.g., forming an arc), or can be aligned along a line. In the concentrically positioned example, the housing can include a motor and the housing can be rotatable about the support arm to bring, individually, the adjustable collimators 20, 22, 24, into alignment with the radiation beam (e.g., by the controller device 28 causing the motor to rotate the housing). In the linear positioned example, the housing can include an actuator (e.g., a linear actuator) that is movably coupled to the support arm and controllable by the controller device 28. Thus, as desired, the controller device 28 can bring, one at a time, the adjustable collimators 20, 22, 24, into alignment with the radiation beam. In some cases, the support arm can be rigid, while in other cases, the support arm can include multiple arms (e.g., at least one lockable joint) so that the housing including the adjustable collimators 20, 22, 24 can all be moved away from the radiation beam (e.g., by pivoting away from the radiation beam so that the radiation beam is not attenuated by any of the collimators 20, 22, 24, such as when the collimator assembly 18 is not in use).

Although in the illustrated non-limiting example of FIG. 1, the collimator assembly 18 is shown as having three adjustable collimators, the number of adjustable collimators for the collimator assembly 18 can be adjusted. For example, in some cases, the collimator assembly 18 can include just the adjustable collimator 20 (or two adjustable collimators), while in other cases, the collimator assembly 18 can include 4, 5, 6, or other additional numbers of adjustable collimators. In some non-limiting examples, the radiation therapy system 100 can have additional collimator assemblies 18. In some configurations, some or all of the collimators 20, 22, 24, can be implemented as an MLC, a bowtie filter, or other dynamically adjustable collimators that are configured to attenuate a radiation beam.

As shown, the controller device 28 is in communication with a table 26, as appropriate. For example, the table 26 is in an adjustable table 26 (e.g., on a robotic arm, or an actuated table), the controller device 28 can control the position (and orientation) of the table 26 relative to the gantry 12 (and thus the radiation beam emitted by the radiation source 14). In some cases, the table 26 can translate into and out of a bore defined by the gantry 12. In other cases, the table 26 can a fixed table 26.

In some non-limiting examples, the controller device 28 can be implemented in different ways. For example, the controller device 28 can include a processor, memory, a display, communication devices, etc. In some cases, the controller device 28 can simply be implemented as a processor. The controller device 28 can communicate with other computing devices and systems. In some non-limiting examples, the controller device 28 can implement some or all of the processes described below.

Figure 2:
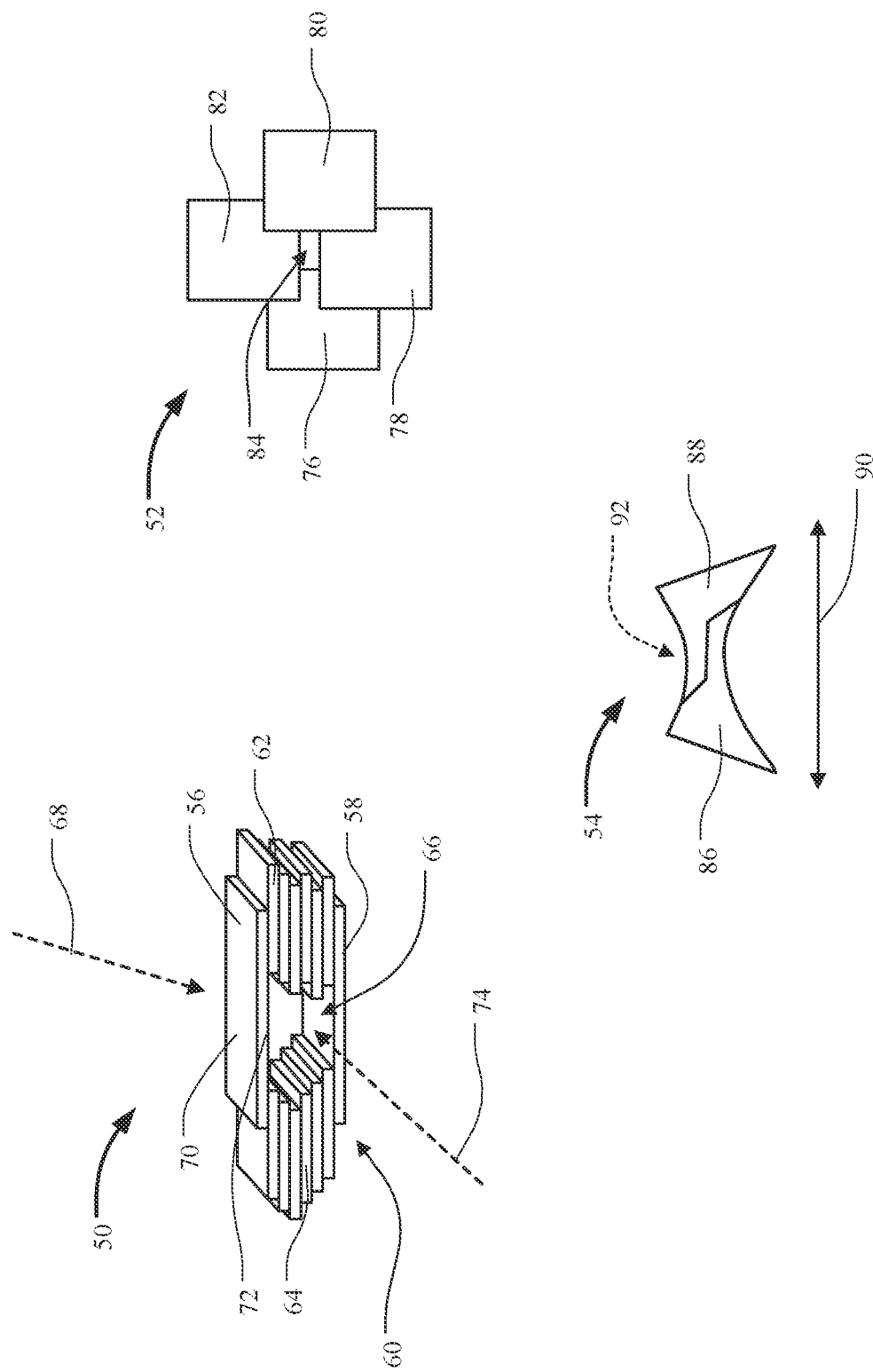
FIG. 2 shows schematic illustrations of MLCs, and an adjustable bowtie filter.
Figure 3:
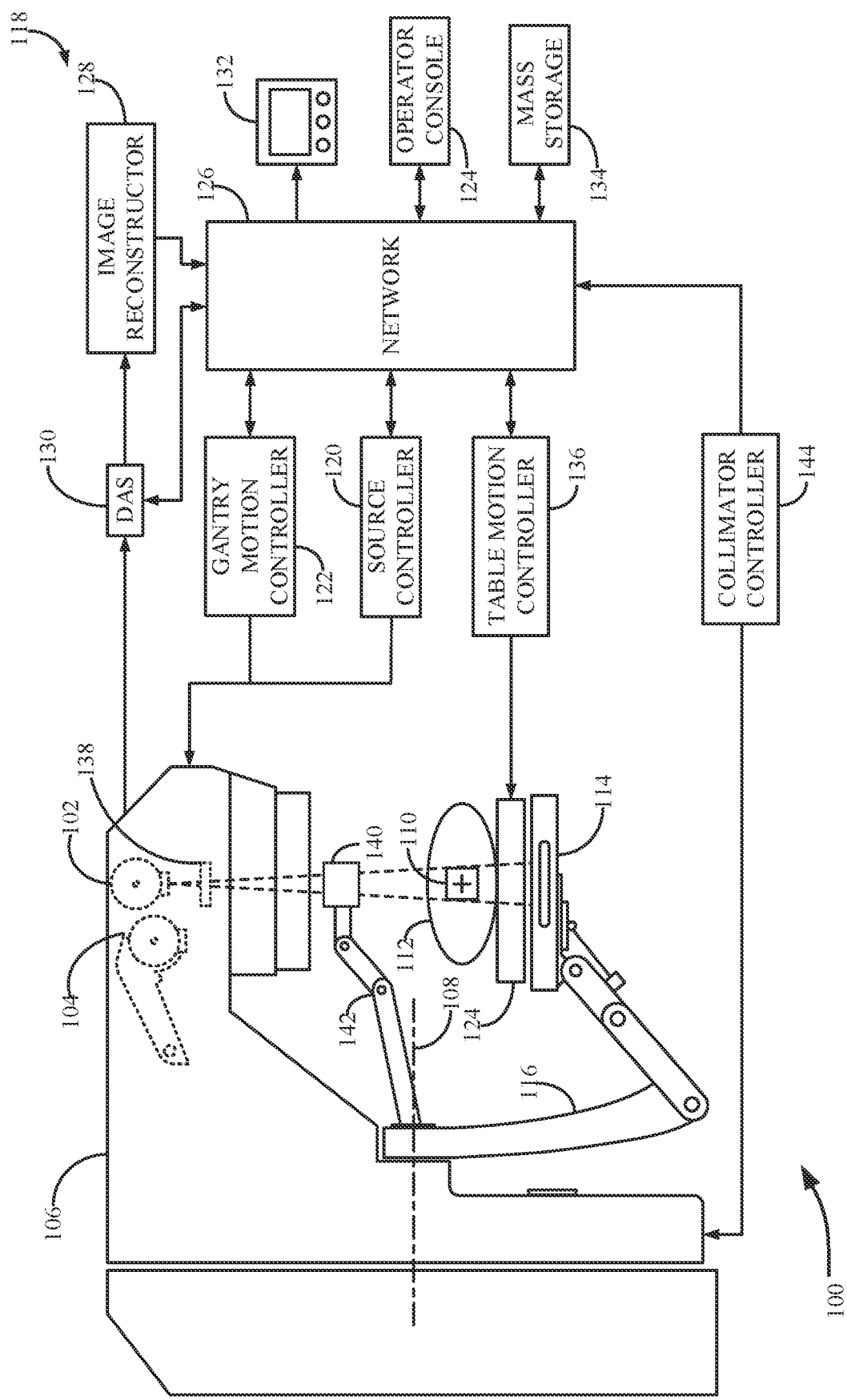
FIG. 3 shows a block diagram of an example radiation therapy system.

FIG. 2 shows schematic illustrations of MLCs 50, 52, and an adjustable bowtie filter 54, each of which are specific implementations of the adjustable collimators 20, 22, 24 of the radiation therapy system 100. Thus, any of the adjustable collimators 20, 22, 24 can be implemented as either of the MLCs 50, 52 or the bowtie filter 54. The MLC 50 can include stationary leaves 56, 58 that are sandwiched about a plurality of independently controllable leaves 60, which includes individually moveable leaves 62, 64. In particular, the stationary leaf 56 is situated above the plurality of independently controllable leaves 60, while the stationary leaf 58 is stated below the plurality of independently controllable leaves 60. The plurality of independently controllable leaves 60 include more individually movable leaves than just the individually moveable leaves 62, 64, but only the leaves 62, 64 have been explicitly mentioned for sake of brevity. As such, the other independently moveable leaves are similar to the individually movable leaves 62, 64.

In the illustrated non-limiting example, there are twelve individually moveable leaves within the plurality of independently controllable leaves 60, however in alternative configurations there could be more or fewer numbers of individually moveable leaves (e.g., 60 leaves with a thickness of 5 mm or less). Similarly, although there are two stationary leaves 56, 58, there can be fewer or larger numbers of stationary leaves. In fact, in some cases, all the leaves of the MLC 50 can be moveable and independently controllable. Although not shown, each independently controllable leaf within the plurality of independently controllable leaves 60 can include respective motors, gears, screws, etc., to move the respective independently controllable leaf, which can be controllable by a controller device (e.g., the controller device 28). Each of the independently controllable leaves 60 is translatable along a common axis (e.g., an axis that's parallel to a longitudinal dimension of the stationary leaf 56). In this way, the collective position of the plurality of independently controllable leaves 60, which defines a void 66 can be adjusted thereby adjusting the radiation attenuation radiation profile of the MLC 50. In particular, because each of the plurality of independently controllable leaves 60 are formed of radiation absorbing materials (e.g., tungsten, lead, etc.), the shape and size of the void 66 can at least partially define the radiation attenuation profile of the MLC 50.

For example, a radiation beam 68 (e.g., emitted from a radiation source) can be mostly directed along an axis that is perpendicular to the longitudinal surface 70 of the stationary leaf 56 (e.g., the axis being the longitudinal axis of the MLC 50). As the radiation beam 68 passes through the thickness of each leaf, the radiation beam 68 is attenuated (e.g., by the independently controllable leaves absorbing the radiation), while as the radiation beam 68 passes through the void 66 (e.g., air) the radiation beam 68 is attenuated at a significantly lower radiation attenuation level (if at all) as compared to the attenuation provided by each leaf. Thus, the shape and size of the void 66, which can be adjusted by the collective positioning of the plurality of independently controllable leaves 60, can adjust the radiation attenuation profile of the MLC 50. As another example, a radiation beam 74 can be mostly directed along an axis that is perpendicular to the lateral surface 72 of the stationary leaf 56 (e.g., the axis being the lateral axis of the MLC 50 that is perpendicular to the longitudinal axis of the MLC 50). As the radiation beam 74 passes through the width of each leaf, the radiation beam 74 is attenuated, while as the radiation beam 74 passes through the void 66, the radiation beam 74 is attenuated at a significantly lower radiation attenuation level (if at all) as compared to the attenuation provided by each leaf. As such, the dimensions of the leaves, the orientation of the radiation beam, and the shape and size of the void 66 can define the radiation attenuation profile of the MLC 50.

The MLC 52 can include independently controllable leaves 76, 78, 80, 82 (e.g., with motors, gears, etc., controllable by a controller device) that are illustrated as being planar, although the shapes of leaves can be different three-dimensional shapes. The independently controllable leaves 76, 78, 80, 82 can translate within their respective plane (e.g., translate along two dimensions defined by the plane), defined by the surface of the respective independently controllable leaves 76, 68, 80, 82. As shown, the collective position of the independently controllable leaves 76, 78, 80, 82 can define the size and shape of a void 84 that can be located in a central region of the MLC 52. For example, the independently controllable leaves 76, 78, 80, 82 can overlap different amounts thereby adjusting the shape and size of the void 84. As a specific example, the leaf 78 can translate towards the leaf 82, which adjusts the opening defined by the void 84 (e.g., the shape of the region having no leaf) and the shape of the void 84 (e.g., how the leaves 76, 78, 80, 82 overlap each other). In some cases, the radiation beam can be emitted along a path that is perpendicular to the top view of the MLC 52, and thus the shape and size of the void 84 can at least partially determine the radiation attenuation profile of the MLC 52 (e.g., including the thicknesses of the leaves 76, 78, 80, 82).

The adjustable bowtie filter 54 can include independently controllable leaves 86, 88 that have the collective shape of a bowtie (e.g., when in a compact configuration), and which can be translated along an axis 90 that can be substantially perpendicular (e.g., deviating by less than 10%) to the path a radiation beam through the bowtie filter 54. The collective positioning of the controllable leaves 86, 88 can define (or in some cases can eliminate) a void 92, which can partially define the radiation attenuation profile of the adjustable bowtie filter 54. Thus, the collective positioning of the independently controllable leaves 86, 88 can adjust the size and shape of the void 92, thereby adjusting the radiation attenuation profile of the adjustable bowtie filter 54. Although the illustrated non-limiting example of the bowtie filter 54 has two independently controllable leaves 86, 88, the adjustable bowtie filter 54 can have additional numbers of independently controllable leaves that can collectively define a bowtie shape (e.g., each of the independently controllable leaves can partially have a bowtie shape).

Referring back to FIG. 1, the controller device 28 can, as described in more detail below, receive a radiation treatment plan. The radiation treatment plan can be determined using ("3D") imaging of the subject (e.g., via, MRI, CT, or other imaging modalities) to create a 3D model of the tumor of the subject. This 3D model of the tumor of the patient can be used to create a radiation treatment plan that is tailored to the specific patient. For example, the radiation treatment plan can define a selection of different radiation beam paths (e.g., the paths being of different strengths, orientations relative to the patient, and emitted of different amounts of time). As a specific example, the controller device 28 can for each radiation beam path, determine a corresponding radiation attenuation profile for the radiation beam path. In particular, each radiation beam path can extend along a 3D line relative to the tumor (or other tissue site) of the patient. Thus, the two-dimensional ("2D") projection of the tumor that is along the 3D line and that faces the tumor can be used to determine a radiation attenuation profile for the respective radiation beam path. In this way, the radiation attenuation profile for each radiation beam path, according to the radiation treatment plan, can be implemented by the collimator assembly 18. For example, the controller device 28 can adjust the attenuation profile for each adjustable collimator 20, 22, 24 to match the radiation attenuation profiles according to the radiation treatment plan (e.g., by adjusting the size and shape of the void of the adjustable collimator to match the shape of the 2D projection for that radiation beam path). In some non-limiting examples, the controller device 28 can dynamically adjust the radiation attenuation profiles of the other adjustable collimators of the collimator assembly that are not being used, as described below.

As shown, the controller device 28 implementing the radiation treatment plan, moves the gantry 12 (and thus the radiation source 14) to the next radiation beam path (e.g., the corresponding orientation) according to the radiation treatment plan. Then, the controller device 28 moves the adjustable collimator (in this case the adjustable collimator 22) that corresponds to the radiation attenuation profile of the next radiation beam path into the proper alignment with the radiation source 14. Then, the controller device 28 can cause the radiation source 14 to emit a radiation beam 30 according to the radiation treatment plan (e.g., the dosage time) through the collimator 16, which attenuates the radiation beam 30 to a first attenuated radiation beam 32. This first attenuated radiation beam 32 is emitted through the adjustable collimator 22 and is attenuated to a second attenuated radiation beam 34 according to the radiation attenuation profile of the adjustable collimator 22. This second attenuated radiation beam 34 is delivered to the patient situated on the table 26. When the adjustable collimator 22 is in use and attenuates the radiation beam, the other adjustable collimators 20, 24 (including other adjustable collimators) of the collimator assembly 18 are not in use. In other words, these other adjustable collimators of the collimator assembly 18 do not attenuate the radiation beam (e.g., the radiation beam 30 or the first radiation attenuated beam 32). In some non-limiting examples, such as when the other adjustable collimators are not in use to attenuate the radiation beam, the attenuation profiles of these other adjustable collimators can be adjusted (e.g., by the controller device 28) according to the radiation beams of the radiation treatment plan. In this way, the time when the adjustable collimators are not in use, can be used to adjust to the next attenuation profiles. In some non-limiting examples, the controller device 28 can cause the next adjustable collimator (e.g., the adjustable collimator 24) to be brought into alignment with the radiation beam used, having already been adjusted to the attenuation profile according to the next radiation beam as defined by the radiation treatment plan. Similarly, the controller device 28 can cause the gantry 12 (and thus the radiation source 14) to move to the orientation as defined by the orientation of the radiation beam for the next radiation beam. Then, the controller device 28 can cause the radiation source to emit another radiation beam along the next radiation beam path, which includes the another radiation beam passing through the next adjustable collimator. This process can be completed for all the radiation beam paths as called for in the radiation treatment plan.

In some non-limiting examples, the average energy of the radiation beam provided to the patient situated on the table 26 can be adjusted by adjusting a duty cycle of at least two collimators (e.g., two adjustable collimators that replace the collimator 16). For example, the duty cycle can be defined by two positions—an on position and an off position. A first collimator can have a first attenuation profile defined as the off position, and the other second collimator can have a second attenuation profile defined as the on position, where the first attenuation profile of the off position attenuates the radiation beam more than the second attenuation profile of the on position. In this way, the controller device 28 can cause (e.g., by activating a motor) the first collimator to be brought into alignment with the radiation beam (with the second collimator out of alignment with the radiation beam) for a first time period, and can cause (e.g., by activating a motor) the second collimator to be brought into alignment with the radiation beam (with the first collimator out of alignment with the radiation beam) for a second period of time. In some cases, the ratio of the second period of time relative to the first period of time can define the duty cycle, which can be adjusted. Additionally, the frequency of the on position can be adjusted as appropriate. In some non-limiting examples, the duty cycle can correspond to a thickness of a tumor (or other tissue) along the 3D line as defined by the radiation beam path. In this way, the duty cycle can be increased thereby delivering a radiation beam having a higher average energy for higher thicknesses of the tumor (and vice versa). In some non-limiting examples, the duty cycle process for adjusting the average energy of the radiation beam can be implemented using a single dynamically adjustable collimator (e.g., in place of the collimator 16). In this case, the on position can be a fully closed position and the off position can be an open position (e.g., that defines a void). In some non-limiting examples, the controller device 28 can radially open and close the adjustable collimator (e.g., using a radially opening and closing iris, such as one having radiation absorbing segments) according to the duty cycle.

Referring to FIG. 1, an example of a radiation therapy system 100. As will be described Adaptations to the radiation system can be made to use the radiation therapy system 100 for a variety of uses including those described by the methods of the present disclosure. The radiation therapy system 100 includes a therapeutic radiation source 102 and an on-board imaging source 104. The radiation source 102 and the on-board imaging source 104 may be housed in the same gantry system 106 or may be mounted orthogonally to the radiation source 102. The radiation therapy system 100 may include any suitable radiation treatment system, including image-guided radiation therapy ("IGRT") systems, intensity-modulated radiation therapy ("IMRT") systems such as intensity-modulated arc therapy ("IMAT") and volumetric modulated arc therapy ("VMAT") systems, an external beam radiotherapy delivery system, such as a linear accelerator ("LINAC"), proton radiotherapy systems, slice by slice photon radiotherapy systems (Tomotherapy), non-isocentric photon radiotherapy systems (Cyberknife®), and isotope based radiotherapy systems (ViewRay™ and GammaKnife®), and the like. In a non-limiting example, the radiation therapy system is a Truebeam™ STX linear accelerator with 6 MV photons and HD-multi-leaf collimator ("MLC"). The treatment beam for the radiation therapy system can be composed of photons, neutrons, electrons, protons, heavy charged particles, or the like. Specific treatment plans can also be designed and delivered in order to evaluate key parameters of each radiotherapy system. Clinically relevant treatment plans can be prepared and utilized for end-to-end testing.

The on-board imaging source 103 may include an x-ray source, a cone-beam computed tomography ("CBCT") system, a computed tomography ("CT") system, a 4DCT system, and the like. Alternatively, the imaging may be performed by a separate diagnostic imaging system. In the illustrated configuration, both the therapeutic radiation source 102 and imaging source 104 are attached adjacent each other and housed at the same end of a rotatable gantry 106, which rotates about a pivot axis 108. The rotatable gantry 106 allows either of the sources, 102 and 104, to be aligned in a desired manner with respect to a target volume 110 in an subject 112 positioned on a table 114 supported by a table support 116.

The rotation of the rotatable gantry 106, the position of table 114, and the operation of the sources, 102 and 104, are governed by a control system 118 of the radiation therapy system 100. The control system 118 includes a source controller 120 that provides power and timing signals to the radiation source 102 and imaging source 104, and receives image data therefrom. A gantry motion controller 122 controls the rotational speed and position of the gantry 106. The control system 118 communicates with an operator console 124 and other parts of a network 126 through a communication system. An image reconstructor 128, receives sampled and digitized image data over the network 126 or from the data acquisition system 130 and performs image reconstruction.

Commands and scanning parameters can be communicated from via the operator console 124. The operator console 124 may include a variety of user interfaces, including a display 132 and may have access to mass storage 134. The operator supplied commands and parameters are used by the computer 109 to provide control signals and information to an imaging controller, and communicate with the source controller 120, the gantry motion controller 122, and a table motion controller 136 to effectuate a radiation therapy process in accordance with a radiation therapy plan.

Still referring now to FIG. 1, the radiation source 102 produces a radiation beam, or "field,", which in some forms may be conical or any other shape, emanating from a focal spot and directed toward the subject 112. In a traditional radiation therapy system, the radiation beam is collimated by a single or stacked collimator 138 that is mounted proximate to and designed to move with the radiation source 102. That is the collimator 138 is secured in the gantry 106 in a fixed position relative to the radiation source 102. The collimator 138 may be a multi-leaf collimator (MLC), for example, constructed of a set of rectangular shutter system blades to form a generally planar "fan" radiation beam centered about a radiation fan beam plane. Each leaf of the collimator 138 is constructed of a dense radio-opaque material such as lead, tungsten, cerium, tantalum, or related alloy.

However, the present disclosure breaks from this traditional architecture of radiation source and collimator to provide a plurality of MLCs that are not positioned to move with the radiation source 102. Instead, a plurality of MLCs 140, such as an array forming an arc about the patient table 114. The MLCs 140 may be affixed on a support 142 that does not require the MLCs to move or rotate with movement or rotation of the radiation source 102. In this way, radiation beams produced by the radiation source 102 can be given a desired beam profile by a plurality of MLCs 140. The radiation source 102 may emit a radiation beam of any shape through each of the plurality of MLCs 140 and each MLC in the plurality of MLCs may be individually adjusted to generate the desired beam profile relative to the beam path formed through that particular MLC and its orientation to the subject 112 and target volume 110. The plurality of MLCs 140 may be in a static position or may move about the pivot axis 108 and/or via adjustment of the support 142. In some non-limiting examples, the support 142 can be positioned on a floor (or other supporting structure).

Thus, a collimator controller 144 may be included. The collimator controller 144 may adjust the position of the plurality of the MLCs and/or may control, separately, actuators to move each of the leaves of each individual MLC. The collimator controller 144 may adjust or reconfigure the leaves of the collimator MLCs 140 rapidly between their open and closed states to either fully attenuate or provide no attenuation to each ray. Gradations in the fluence of each ray, as needed for the fluence profile, are obtained by adjusting the relative duration during which each leaf is in the closed position compared to the relative duration during which each leaf is in the open position for each gantry angle.

The ratio between the closed and open states or the "duty cycle" for each leaf affects the total energy passed by a given leaf at for each beam path, which can be defined, for example, relative to each positon or gantry angle, θ, and thus controls the average fluence of each ray. The ability to control the average fluence at each gantry angle, θ, permits accurate control of the dose provided by the radiation beam through the irradiated volume of the subject 112 by therapy planning methods to be described below. The collimator controller 144 also connects with the network 126 to allow program control of the collimator controller 144, such as from the operator console 124 or other computer to effectuate the therapy plan.

Figure 4:
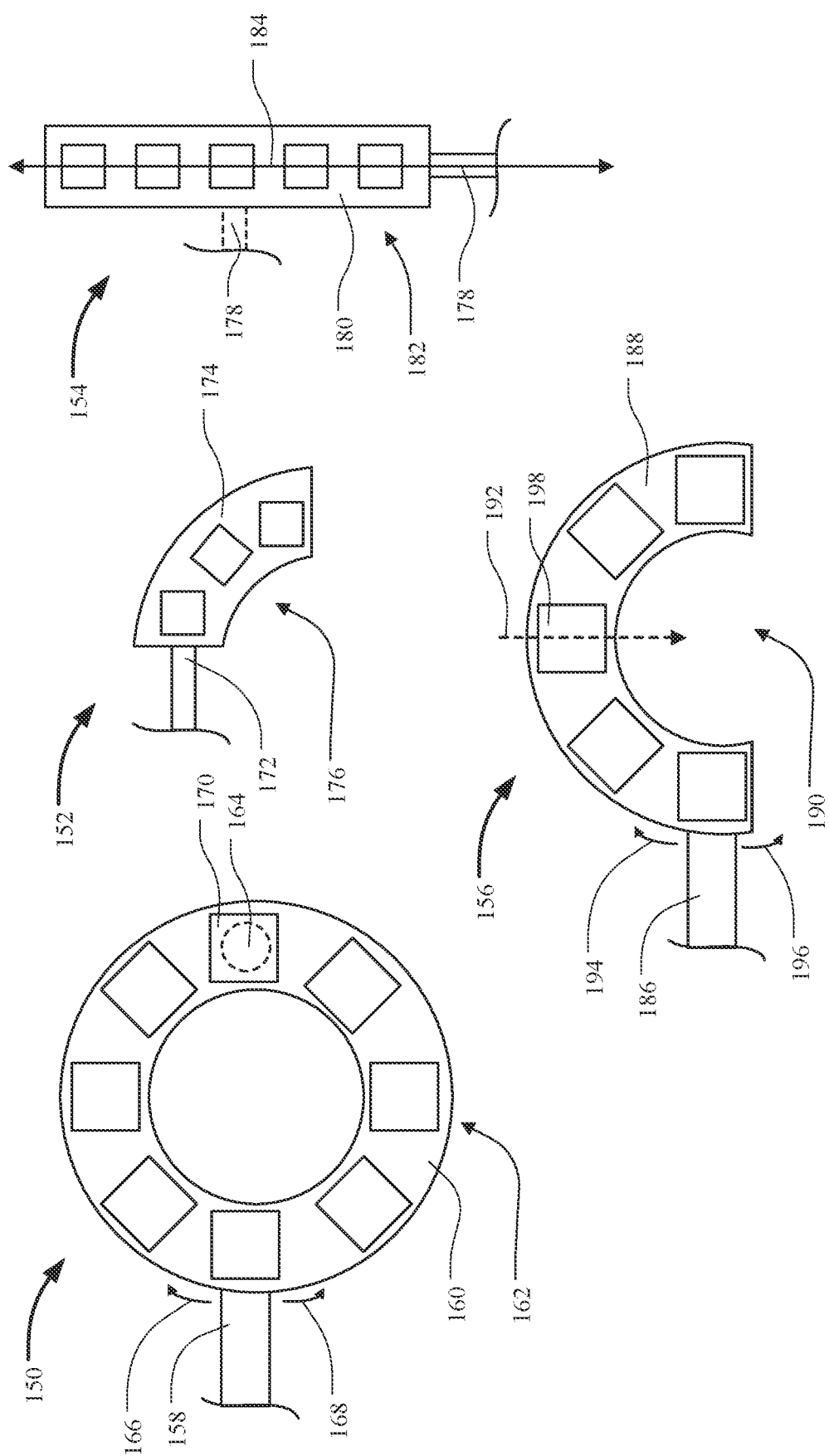
FIG. 4 shows schematic illustrations of different non-limiting examples of collimator assemblies, each having a plurality of adjustable collimators.

FIG. 4 shows schematic illustrations of different non-limiting examples of collimator assemblies 150, 152, 154, 156, each having a plurality of adjustable collimators (e.g., MLCs), which can be implemented as the plurality of MLCs 140 of the radiation therapy system 100. The collimator assembly 150 can include a support arm 158, a rotatable housing 160 having a donut shape (or cylinder shape), an a plurality of adjustable collimators 162. As shown, the collimator assembly 150 is rotatable about an axis that is substantially perpendicular to an elongate axis of the support 158 and that is substantially parallel to a radiation beam path of a radiation beam 164. For example, as shown, the housing 160 that includes and supports the plurality of adjustable collimators 162 is rotatable in one rotational direction 166 about the axis, and is rotatable in an opposite second rotational direction 168 about the axis. In some cases, a controller device can cause a motor to rotate the housing in either of the direction 166, 168. As shown, one end of the support arm 158 is coupled to the housing 160 (e.g., so that the housing 160 can still rotate) and the an opposing end of the support arm 158 can be coupled to a portion of the rotatable gantry 106. In other configurations, the opposing end of the support arm 158 can be coupled to a robot arm (e.g., the support arm 158 being the end effector of the robot arm). As also detailed above, the radiation attenuation profile of each of the plurality of adjustable collimators 162 can be different (e.g., to correspond to the radiation treatment plan). For example, as shown, the radiation beam 164 can pass through a top surface of an adjustable collimator 170, which is one of the plurality of adjustable collimators 162. As also shown, the plurality of adjustable collimators are positioned concentrically around the rotatable axis of the housing 160, such that adjacent adjustable collimators define an arc length, and the sum of the arc lengths can be 360 degrees. In other cases, the sum of the arc lengths can be less than 360 degrees.

The collimator assembly 152 also includes a support arm 172 coupled to a housing 174 having an arc shape, and a plurality of adjustable collimators 176. In some cases, similarly to the housing 160, the housing 174 can rotate about a similar axis as the housing 160 and can be caused to move via a motor. In some cases, the support arm 172 can be coupled to the rotatable gantry 106, while in other cases, the support arm 172 can be coupled to a robot arm in a similar manner as the support arm 158.

The collimator assembly 154 also includes a support arm 178 coupled to a housing 180, and a plurality of adjustable collimators 182. As shown, the plurality of adjustable collimators 182 are coupled to the housing 180, and are positioned and aligned along a longitudinal axis 184 of the housing 180. In some non-limiting examples, the housing 180 can be translated along the longitudinal axis 184 so that each adjustable collimator of the plurality of adjustable collimators 182 can individually be brought into alignment with the radiation beam. For example, an actuator that moveably couples together the support arm 178 to the housing 180, or that advances the support arm 178 with the housing 180 coupled thereto, can advance or retract the actuator thereby translating the housing 180 (and thus the plurality of adjustable collimators 182) along the axis 184. In some cases, one end of the support arm 178 can be coupled to the housing 180 so that a portion of the support arm 178 extends along the axis 184. In other cases, the one end of the support arm 178 can be coupled to the housing 180 so that a portion of the support arm 178 extends along an axis that is substantially perpendicular to the axis 184 (e.g., indicated by the dotted support arm 178). Similarly to the other configurations, the opposing end of the support arm 178 can be coupled to the rotatable gantry 106, or a robot arm.

The collimator assembly 156 also includes a support arm 186 coupled to a housing 188, and a plurality of adjustable collimators 190. As shown, the plurality of adjustable collimators 190 are coupled to the housing 188 that has a semi-circular (donut) shape, and are situated circumferentially about an axis that is perpendicular to the radiation beam 192. In some non-limiting examples, the housing 188 of the collimator assembly 156 is also rotatable about this axis along a first rotational direction 194 and a second rotational direction 196 to selectively bring each of the adjustable collimators into alignment with the radiation beam 192 as desired. For example, in the illustrated non-limiting example, the radiation beam 192 that is directed at a peripheral surface of the housing 188, passes through an adjustable collimator 198 of the plurality of adjustable collimators 190 and is attenuated according to the radiation attenuation profile of the adjustable collimator 198.

FIG. 5 shows a schematic illustration of a 3D volume of a tumor 200 of a patient, and three different two-dimensional ("2D") projections 202, 204, 206 of the 3D volume of the tumor 200 to be used to determine a radiation attenuation profile for each adjustable collimator. The 2D projection 202 is the 2D projection taken about a front view of the 3D volume of the tumor 200 (e.g., where the 2D projection is taken from a 3D line intersecting the front view). The 2D projection 204 is the 2D projection taken from a side view of the 3D volume of the tumor 200. The 2D projection 206 is the 2D projection taken from another side view of the 3D volume of the tumor 200. Although three different 2D projections 202, 204, 206 have been described, other numbers of 2D projections can be utilized and taken along different desired radiation beam paths (e.g., orientations, 3D lines, etc.).

FIG. 6 shows a schematic illustration of an example of a collimator assembly 210. The collimator assembly 210 has a housing 212, and adjustable collimators 214, 216, 218 coupled to the housing 212. FIG. 6 visually depicts the attenuation profiles corresponding to the 2D projection of the tumor for those particular radiation beam paths (e.g., according to a radiation treatment plan). For example, as shown, the attenuation profile of the adjustable collimator 214 is adjusted to be based on the 2D projection 202. In particular, the shape of a void 220 of the adjustable collimator 214 substantially matches the shape of the 2D projection (e.g., deviating by less than 10%). In some cases, the size of the void 220 can be based on the intended distance from the radiation source to the tumor along this radiation beam path. As another example, the attenuation profile of the adjustable collimator 216 is adjusted to be based on the 2D projection 204. In particular, the shape of a void 222 of the adjustable collimator 216 substantially matches the shape of the 2D projection (e.g., deviating by less than 10%). In some cases, the size of the void 222 can be based on the intended distance from the radiation source to the tumor along this radiation beam path. As yet another example, the attenuation profile of the adjustable collimator 218 is adjusted to be based on the 2D projection 206. In particular, the shape of a void 224 of the adjustable collimator 218 substantially matches the shape of the 2D projection (e.g., deviating by less than 10%). In some cases, the size of the void 224 can be based on the intended distance from the radiation source to the tumor along this radiation beam path. As described below, a computing device can cause the collimator assembly 210 to selectively align a single particular adjustable collimator 214, 216, 218 based on the current radiation beam path. For example, if the radiation beam path is the same orientation used to determine the 2D projection 202 (e.g., the radiation beam path directed at the front view of the tumor), the computing device cause the adjustable collimator 214 to be brought into alignment with the radiation beam thereby attenuating the radiation beam according to the attenuation profile of the adjustable collimator 214 (e.g., that corresponds close to the 2D projection at that radiation beam orientation).

Figure 7A:
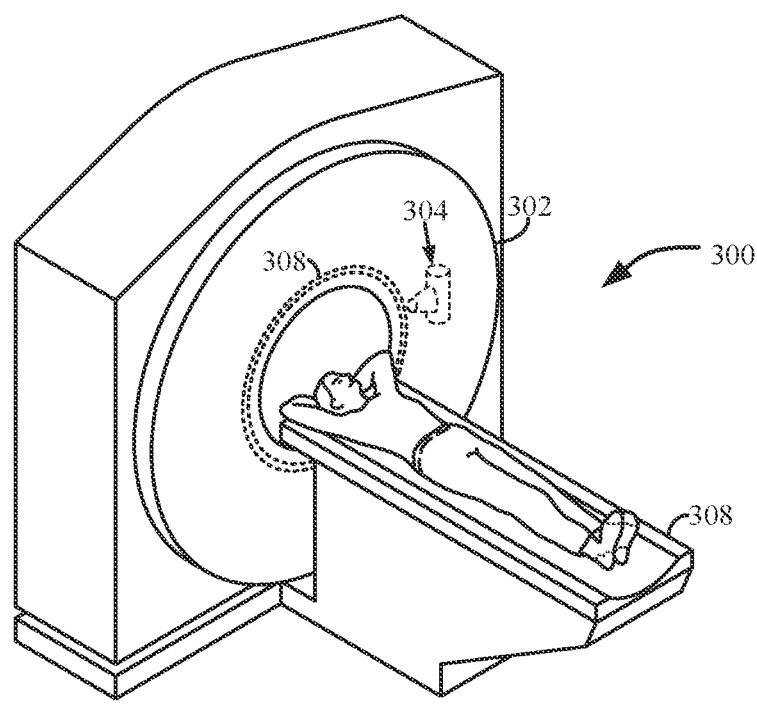
FIG. 7A shows a perspective view of a gantry-based RT system including a plurality of multi-leaf collimators in accordance with the present disclosure.

Referring particularly now to FIG. 7A, an example of another therapy system 300, which includes a circular gantry 302, is illustrated. In this case, the gantry 302 supports a radiation source 304 and a plurality of MLCs 306. The x-ray source 304 projects a radiation beam, which may be a fan-beam or cone-beam through the MLCs 306. As illustrated, the MLCs 306 may be formed as a full circle that surrounds a patient table 308. However, the MLCs 306 may also be formed as an arc, line, or other shape. As the source 304 moves about the gantry 302, the radiation beam travels through each (or some) of the plurality of MLCs 306 to generate the desired beam shape or profile. The plurality of MLCs 306 can be positionally fixed or can be rotated about the gantry 302. In one non-limiting configuration, the MLCs 306 may be rotated, such as in a direction opposite the direction of the x-ray source 304 or in a direction of the x-ray source 304. In some non-limiting examples, the patient table 308 can be implemented as other patient supporting chairs or tables described above.

Figure 7B:
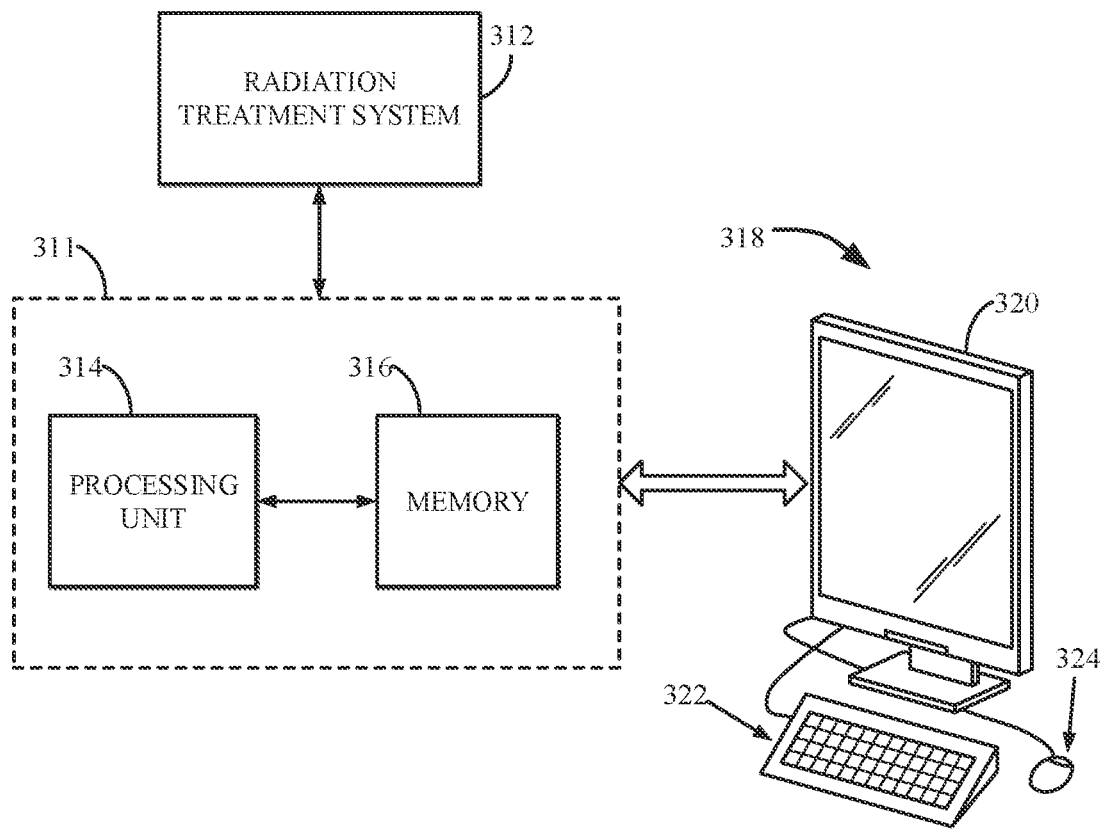
FIG. 7B shows a block diagram of a RT system of FIG. 7A.

Referring particularly now to FIG. 7B, an example block diagram is provided of a radiation treatment planning system 311 is illustrated. The radiation treatment planning system 311 is preferably in communication with one or more radiation treatment systems 312, such as described with respect to the previous figures. The radiation treatment system of FIG. 7B is compatible with all the described radiation treatment systems of this disclosure to implement a radiation treatment plan.

The radiation treatment planning system 311 generally includes a processing unit 314 and a memory 316 that is operably coupled to the processor unit 314. As an example, the processor unit 314 can be a commercially available computer processor, such as those described above. The processor unit is configured to carry out one or more of the steps of the methods described above. As an example, the memory 316 can include a plurality of memory elements, or can include a single memory element. In general, the memory 316 is configured to store information regarding patient data, a clinical treatment plan, calibration curves, dose measurements obtained from the dosimeter and cylindrical diode-array QA phantom, and so on.

Preferably, the radiation treatment planning system 311 includes, or is otherwise in communication with, a user interface 318. As an example, the user interface 318 provides information to a user, such as a medical physicist. For example, the user interface 318 can include a display 320 and one or more input devices, such as a keyboard 322 and mouse 324.

Figure 8:
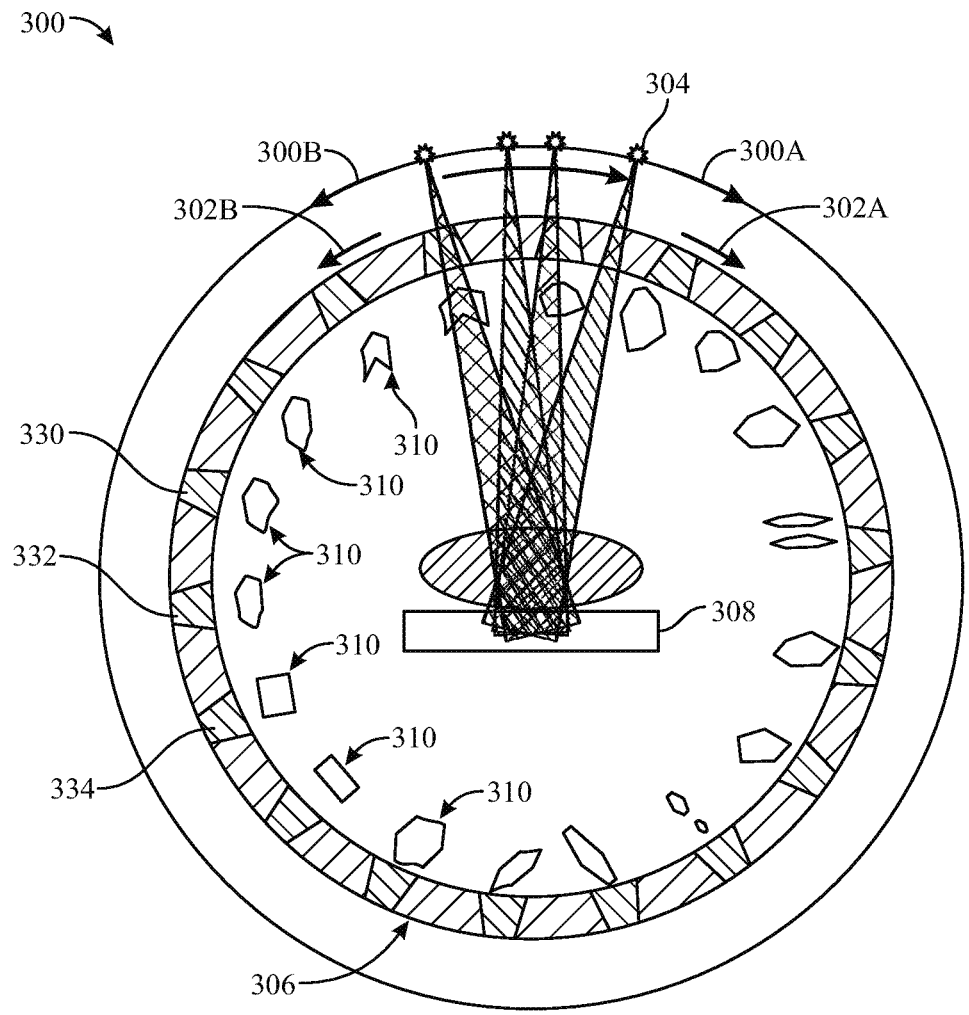
FIG. 8 shows a schematic diagram of the RT system of FIG. 2A showing the gantry and multi-leaf collimator ("MLC") system in accordance with the present disclosure.

Referring now to FIG. 8 a schematic example of the radiation system 300 of FIG. 7A in operation is illustrated. The radiation therapy system 300 includes the gantry 302 that facilitates rotation of the source 304 about the patient bed 308. The plurality of MLCs 306 are positioned between the source 304 and the patient table 308. In one non-limiting example, the plurality of MLCs 306 may form a ring shape about the gantry. In another non-limiting example, the plurality of MLCs 306 may form the shape of an arc or other orientation, including a linear orientation. The arc may have a varying length based on a target region of the radiation therapy system 300. For example, the size, location, and type of target region are all factors that contribute to determining the length the arc. The length of the arc may also be determined based on the patient table 308. For example, the length is varied within a range of an acute angle to an obtuse angle. In some non-limiting examples, based on the target region, a full ring of the MLCs may not be required for an effective radiation therapy system.

As shown, each MLC within the plurality of MLCs 306 can have their own different radiation attenuation profile. In this case, the plurality of MLCs 306 define a plurality of different void shapes 310, where each void shape is defined by each MLC, and which can be adjustable. For example, the plurality of MLCs 306 can include collimators 330, 332, 334. The collimators 330, 332, 334 can be adjustable (e.g., by a computing device) to adjust the radiation attenuation profile of each collimator. For example, each collimator can be independently controlled to each realize different void shapes and, thereby, achieve different beam shapes. The shapes of each of the collimators 330, 332, 334 is determined based on the radiation therapy plan, the size and shape of the target, and the like. For example, tumors having different shapes, sizes, locations, depths, and anatomies require each of the first, second, and third collimators 330, 332, 334 to define different void shapes. For example, the voids of the first, second, and third collimators 330, 332, 334 can be adjusted in shape based on their orientation (or intended orientation) with respect to the target or tumor.

In some non-limiting examples, the system 311 may be used to create a radiation therapy plan to control the gantry, the radiation therapy source 304, and the plurality of MLCs 306. The radiation therapy plan may be a rotational FLASH IMRT plan. In this case, the radiation ray source 304 is switched on when it is aligned with a desired MLC, which forms a specific aperture at the specific angle. The shape of the aperture is determined by Rotational direct Aperture optimization with a Decoupled ring-collimator (ROAD) FLASH optimization. The MLC ring can be static or rotate at a desynchronized speed to expose the source to different MLC void shapes, or in other words different MLC apertures.

As one non-limiting example, the radiation therapy source 304 is positioned according to the plan at a first collimator of the plurality of MLCs 306. The radiation therapy source 304 can then be activated to emit a radiation beam through a first collimator to deliver a first radiation beam shape. The radiation therapy source 304 can then be rotated in a first direction 300A, towards a second collimator of the plurality of MLCs 306 to emit a radiation beam through the second collimator. The radiation therapy source 304, each time it emits a radiation beam, is positioned to emit the radiation bean through one of the plurality of MLCs at a time. Each collimator in the plurality of MLCs can be independently configured to change an orientation and shape of each of the plurality of MLCs based on the radiation beam profile for the particular beam path.

The radiation therapy source 304 can be rotated in a second direction 300B. As the radiation therapy source 304 is rotated, the plurality of MLCs can be stationary. As another non-limiting example, as the radiation therapy source 304 is rotated, the plurality of MLCs 306 can also be rotated about the gantry 302 in a first direction 302A or the second direction 302B. In one non-limiting, if the radiation source 304 rotates in a first direction 300A, then the plurality of MLCs may be rotated in a second direction 302B that is opposite to the first direction 300A. Alternatively, the plurality of MLCs can be rotated in the same direction as the radiation therapy source 304. The direction of rotation of the radiation therapy source and the plurality of MLCs can be changed independently to reach desired intersection points. The intersection point is at an intersection of the radiation therapy source 304 and the beginning of the plurality of MLCs 306 or a particular MLC in the plurality of MLCs.

Figure 9:
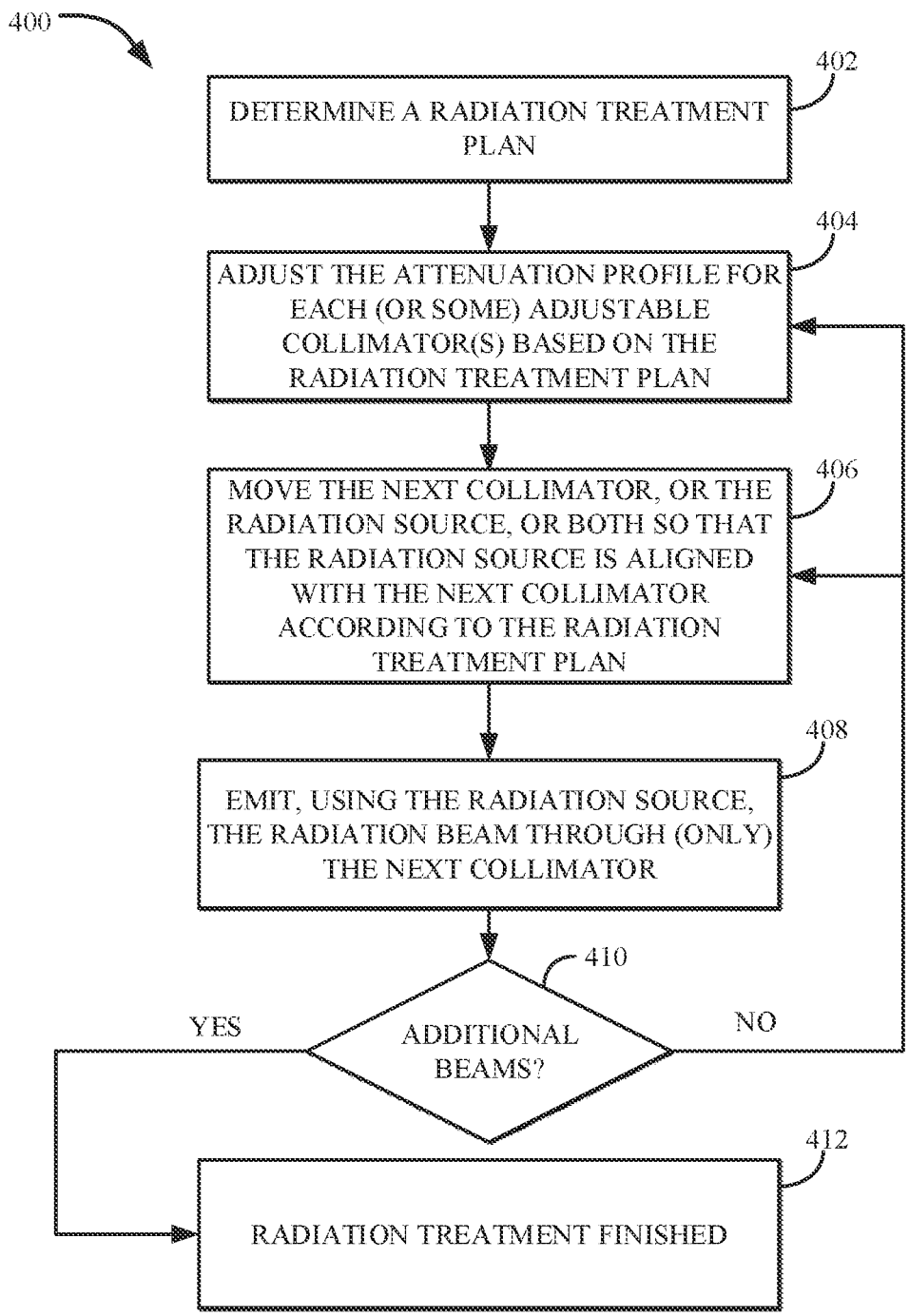
FIG. 9 shows a flowchart of a process for implementing a radiation therapy treatment for a patient.
Figure 10:
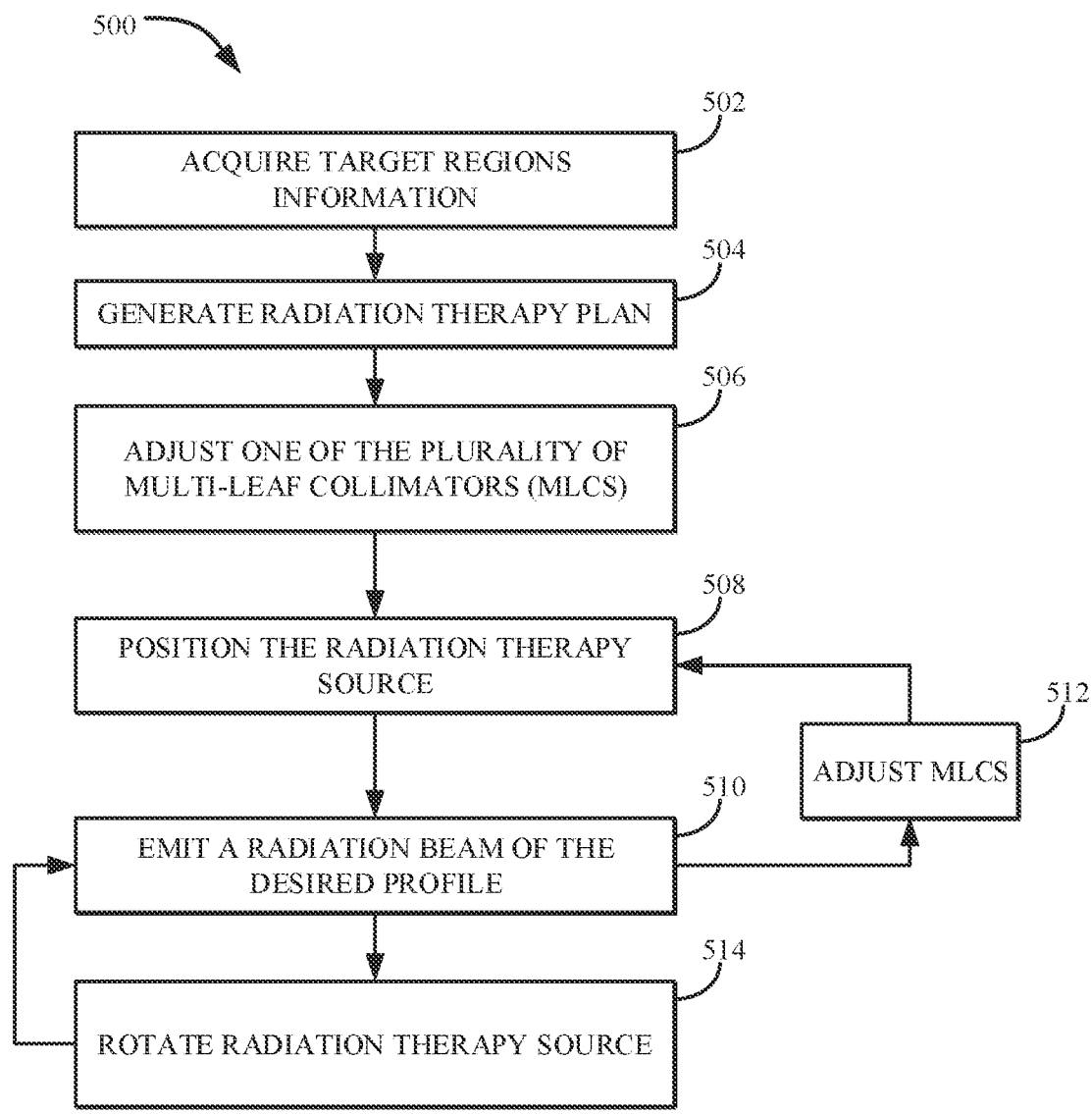
FIG. 10 shows another flowchart setting forth the steps of for delivering radiation therapy to a patient in accordance with the present disclosure.

FIG. 9 shows a flowchart of a process 400 for implementing a radiation therapy treatment for a patient, some or all of which (as appropriate) can be implement on one or more computing devices (e.g., the controller device 28). At 402, the process 400 can include a computing device determining a radiation treatment plan for the patient. In some cases, this can include acquiring 3D imaging data from the patient, generating a 3D model of a tumor of the subject (or other tissue site of a patient), determining which radiation beam paths following particular orientations relative to the patients should be used, determining for each radiation beam path the desired radiation dose to be delivered. In some non-limiting examples, once each radiation beam path has been determined, the computing device can determine the 2D projection of the 3D model of the tumor along each radiation beam path (e.g., along the orientation or the radiation source relative to the patient).

At 404, the process 400 can include a computing device adjusting each radiation attenuation profile for each (or some) adjustable collimator(s) (e.g., an MLC) of the plurality of adjustable collimators according to a respective radiation beam path according to the radiation treatment plan. For example, the computing device can assign each radiation beam path to each adjustable collimator, and then adjust the respective radiation attenuation profile for each adjustable collimator according to its assigned radiation beam path. In some cases, this can include the computing device adjusting the size or shape of the void of each adjustable collimator to match the 2D projection of the tumor for that assigned radiation beam path. In some non-limiting examples, there may be more radiation beam paths than adjustable collimators. In this case, as described below, once an adjustable has been used to deliver radiation to a patient, it can be adjusted to a different radiation attenuation profile according to a different corresponding radiation beam path (e.g., the adjustable collimators can be adjusted on the fly when not in use).

At 406, the process 400 can include a computing device moving the next collimator, or the radiation source, or both, so that the radiation source (e.g., the radiation beam) is aligned with the next collimator according to the next radiation beam path of the radiation treatment plan (e.g., the next collimator assigned and adjusted based on the next radiation beam path). In some non-limiting examples, the computing device can move the radiation source (e.g., by rotating the gantry) to the orientation defined by the next radiation treatment path. In some cases, the computing device can move the next collimator into alignment with the radiation source. In some cases, such as with the plurality of collimators being fixed, the computing device can move the radiation source to align the next collimator with the radiation source.

At 408, the process 400 can include a computing device causing the radiation source to emit a radiation beam through (only) the next collimator to attenuate the radiation beam according to the attenuation profile of the next collimator. In some non-limiting examples, the computing device only emits the radiation beam when the radiation source is aligned along the next radiation beam path and the radiation source is aligned with the next collimator. In some non-limiting examples, because the other collimators may not have been already set according to their assigned radiation beam path, while the radiation source emits the radiation beam the computing device can adjust the radiation attenuation profiles of the other collimators.

At 410, the process 400 can include a computing device determining whether or not additional radiation beam paths exist according to the radiation treatment plan. If at 410, the computing device determines that there are additional radiation beam paths to be implemented, process 400 can proceed back to blocks 404, 406, or both. For example, the computing device can proceed back to block 406 to implement the next radiation beam path according to, for example, a listing of radiation beam paths still yet (and required) to be delivered to a patient. In some non-limiting examples, a computing device prevents the radiation source from emitting a radiation beam when the radiation source is moving, when the collimator assembly (or collimator) is moving, or when both the radiation source and the collimator assembly are moving. In some cases, process 400 can proceed back to block 406 to adjust the radiation attenuation profiles of the collimators. For example, if the delivery of the radiation beam according to the previous radiation beam path was not desired (e.g., corresponding as appropriate to the radiation treatment plan), other radiation beam paths can be used to compensate for any failure to dose the desired portions of the tumor. As another example, the previous collimator that was just used is now free to be adjusted to a different radiation attenuation profile according to a different radiation beam path. If at 410, the process 400 determines that there are on more radiation beam paths to be implemented, process 400 can proceed to 412 to finished the radiation treatment.

Referring now to FIG. 5, a flowchart setting forth the steps of a non-limiting example method for delivering radiation therapy to a patient of the present disclosure is illustrated. Target region data is acquired as indicated at step 502. The target region data can include size, shape, and volume of the target region, among other information. As one non-limiting example, the target region is a tumor on a patient and the target region data includes the type of tumor, anatomy of the tumor and surrounding tissue, depth of the tumor. Each of these features of the target region aid in developing a beam profile.

A radiation therapy plan is then developed at step 504. The plan may include a desired beam profile at each beam path. Thus, the desired beam profile may be used to adjust or configure the plurality of MLCs. The controller configures the radiation therapy source to deliver the radiation therapy to the patient based on the desired beam paths using the MLCs to deliver the desired beam profile along each beam path. As a non-limiting example, the desired beam profile is designed to target the tumor and avoid the radiation beam from being directed at the normal tissue surrounding the tumor. The desired beam profile is developed by careful utilization of the target region to determine each aspect of the profile.

The therapy plan may also include a course of action for the plurality of MLCs and the radiation therapy source to achieve a desired result. For example, a dosage for the radiation therapy source, time and length of dosage, and shape of the plurality of MLCs may be part of or derived from the radiation therapy plan. The dosage and length for the radiation therapy source is based on the target data and the anatomy of the patient. As one non-limiting example, the dose may be a high-dose and the plan may reflect a FLASH treatment protocol.

Each of the plurality of MLCs can be configured to be a specific shape based on anatomy of the patient as well as the anatomy of the target and surrounding tissue using ROAD. The shapes of the plurality of MLCs are also determined based on similar factors as is the dosage aspects. As one non-limiting example, the plurality of MLCs can include two multi-leaf collimators, each being a different shape based on size and location of the target and the patient. Each of the plurality of MCLs can be individually configured to be a different shape. As yet another non-limiting example, the plurality of MLCs can include collimators that are oriented next to each other to form the arc or ring.

The shape of at least one of the plurality of MLCs according to the desired beam profile are adjusted, as indicated at step 506. A controller configured the at least one of the plurality of MLCs to the shape of the desired beam profile. Each of the plurality of MLCs are individually adjusted based on the desired beam profile by the controller. The controller can further be configured to adjust the radiation therapy source.

The radiation therapy source is positioned above the at least one of the plurality of MLCs, as indicated at step 508. The radiation therapy source can be controlled by the controller to move the radiation therapy source. Positioning the radiation therapy source above one of the plurality of MLCs provides the radiation therapy source to be in line with the plurality of MLCs.

The radiation therapy source emits a radiation beam through the at least one of the plurality of MLCs to achieve the desired beam profile, as indicated at step 510. Optionally, the MLCs may be adjusted between selected instances of beam delivery, as indicated at step 512, or the radiation source may be rotated to the next location without adjustment to the MLCs, as indicated at step 514. This process repeats until the radiation therapy plan is completed.

The present disclosure has described one or more preferred non-limiting examples, and it should be appreciated that many equivalents, alternatives, variations, and modifications, aside from those expressly stated, are possible and within the scope of the invention.

It is to be understood that the disclosure is not limited in its application to the details of construction and the arrangement of components set forth in the following description or illustrated in the following drawings. The disclosure is capable of other non-limiting examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise limited or defined, discussion of particular directions is provided by example only, with regard to particular non-limiting examples or relevant illustrations. For example, discussion of "top," "front," or "back" features is generally intended as a description only of the orientation of such features relative to a reference frame of a particular example or illustration. Correspondingly, for example, a "top" feature may sometimes be disposed below a "bottom" feature (and so on), in some arrangements or non-limiting examples. Further, references to particular rotational or other movements (e.g., counterclockwise rotation) is generally intended as a description only of movement relative a reference frame of a particular example of illustration.

In some non-limiting examples, aspects of the disclosure, including computerized implementations of methods according to the disclosure, can be implemented as a system, method, apparatus, or article of manufacture using standard programming or engineering techniques to produce software, firmware, hardware, or any combination thereof to control a processor device (e.g., a serial or parallel general purpose or specialized processor chip, a single- or multi-core chip, a microprocessor, a field programmable gate array, any variety of combinations of a control unit, arithmetic logic unit, and processor register, and so on), a computer (e.g., a processor device operatively coupled to a memory), or another electronically operated controller to implement aspects detailed herein. Accordingly, for example, non-limiting examples of the disclosure can be implemented as a set of instructions, tangibly embodied on a non-transitory computer-readable media, such that a processor device can implement the instructions based upon reading the instructions from the computer-readable media. Some non-limiting examples of the disclosure can include (or utilize) a control device such as an automation device, a special purpose or general purpose computer including various computer hardware, software, firmware, and so on, consistent with the discussion below. As specific examples, a control device can include a processor, a microcontroller, a field-programmable gate array, a programmable logic controller, logic gates etc., and other typical components that are known in the art for implementation of appropriate functionality (e.g., memory, communication systems, power sources, user interfaces and other inputs, etc.).

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally it should be appreciated that a carrier wave can be employed to carry computer-readable electronic data such as those used in transmitting and receiving electronic mail or in accessing a network such as the Internet or a local area network (LAN). Those skilled in the art will recognize that many modifications may be made to these configurations without departing from the scope or spirit of the claimed subject matter.

Certain operations of methods according to the disclosure, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular non-limiting examples of the disclosure. Further, in some non-limiting examples, certain operations can be executed in parallel, including by dedicated parallel processing devices, or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as non-limiting examples of the disclosure, of the utilized features and implemented capabilities of such device or system.

As used herein, unless otherwise defined or limited, ordinal numbers are used herein for convenience of reference based generally on the order in which particular components are presented for the relevant part of the disclosure. In this regard, for example, designations such as "first," "second," etc., generally indicate only the order in which the relevant component is introduced for discussion and generally do not indicate or require a particular spatial arrangement, functional or structural primacy or order.

As used herein, unless otherwise defined or limited, directional terms are used for convenience of reference for discussion of particular figures or examples. For example, references to downward (or other) directions or top (or other) positions may be used to discuss aspects of a particular example or figure, but do not necessarily require similar orientation or geometry in all installations or configurations.

This discussion is presented to enable a person skilled in the art to make and use non-limiting examples of the disclosure. Various modifications to the illustrated examples will be readily apparent to those skilled in the art, and the generic principles herein can be applied to other examples and applications without departing from the principles disclosed herein. Thus, non-limiting examples of the disclosure are not intended to be limited to non-limiting examples shown, but are to be accorded the widest scope consistent with the principles and features disclosed herein and the claims below. The following detailed description is to be read with reference to the figures, in which like elements in different figures have like reference numerals. The figures, which are not necessarily to scale, depict selected examples and are not intended to limit the scope of the disclosure. Skilled artisans will recognize the examples provided herein have many useful alternatives and fall within the scope of the disclosure.

Various features and advantages of the disclosure are set forth in the following claims.

What is claimed is:

1. A radiation therapy system comprising:
   a radiation source configured to emit a radiation therapy beam toward a patient having a tumor to effectuate a radiation therapy process;
   a plurality of dynamically-adjustable collimators, each of the dynamically-adjustable collimators configured to be independently controlled to create a respective attenuation profile at each of the dynamically-adjustable collimators; and
   a controller device configured to:
      adjust the respective attenuation profile at each of the dynamically-adjustable collimators based on a shape of the tumor relative to a respective beam path defined by a path followed from the radiation source through a respective dynamically-adjustable collimator and to the tumor of the patient; and
      effectuate the radiation therapy process by controlling at least one of a position of the radiation source or the plurality of dynamically-adjustable collimators relative to the patient to deliver the radiation therapy beam through each of the plurality of dynamically-adjustable collimators to match a shape of the radiation therapy beam to the shape of the tumor relative to the respective beam path defined by the path followed from the radiation source through a respective dynamically-adjustable collimator and to the tumor of the patient.

2. The system of claim 1, wherein only one of the dynamically-adjustable collimators are used at a time to attenuate the radiation beam according to their respective attenuation profiles.

3. The system of claim 2, wherein the radiation source is configured to move out of alignment with a first dynamically-adjustable collimator and into alignment with a second dynamically-adjustable collimator while the first and second dynamically-adjustable collimators are stationary, the first and second dynamically-adjustable collimators being part of the plurality of dynamically-adjustable collimators.

4. The system of claim 2, wherein each radiation attenuation profile of each dynamically-adjustable collimator is different, and
   wherein each radiation attenuation profile of each dynamically-adjustable collimator is based on a two-dimensional projection of a three-dimensional representation of a tumor of the patient at different orientations about the patient.

5. The system of claim 1, wherein each dynamically-adjustable collimator is a multi-leaf collimator (MLC) having a plurality of individually controllable leaves.

6. The system of claim 5, wherein the controller device is configured to adjust the positions of the independently controllably leaves that define the respective radiation attenuation profile for each MLC, based on a radiation treatment plan for the patient.

7. The system of claim 1, further comprising a table configured to support the patient,
   wherein the plurality of dynamically-adjustable collimators are oriented concentrically about the table,
   wherein each of the dynamically-adjustable collimators are located at a different concentric position about the table, and
   wherein each pair of adjacent MLCs defines a concentric arc therebetween, and the sum of the concentric arcs spans a concentric arc length about the patient.

8. The system of claim 1, further comprising:
a robotic arm having a number of articulable joints, the robotic arm being in communication with and controllable by the controller device; and
a housing that secures and couples together the plurality of dynamically-adjustable collimators, the housing being coupled to the robot arm, and
wherein the controller device is configured to adjust the positioning of the robotic arm relative to the radiation source, thereby selectively aligning a given dynamically-adjustable collimator with the radiation beam.

9. The system of claim 1, wherein a first dynamically-adjustable collimator of the plurality of dynamically-adjustable collimators includes a plurality of independently controllable leaves, and
wherein the collective positioning of the plurality of independently controllable defines a void of the first dynamically-adjustable collimator, which defines the attenuation profile of the first dynamically-adjustable collimator.

10. The system of claim 1, wherein the radiation therapy beam has an ultra-high dose and lasts for a short duration, the ultra-high dose being at least 100 Gy/s, and the short duration being between 0.01 seconds and 0.5 seconds.

11. A computer-implemented method for providing radiation treatment for a patient, the method comprising:
receiving, using one or more computing devices, a radiation treatment plan for the patient;
adjusting for a plurality of adjustable collimators, using the one or more computing devices, each attenuation profile of each adjustable collimator of the plurality of adjustable collimators based on the radiation treatment plan, the plurality of adjustable collimators including a first adjustable collimator and a second adjustable collimator;
moving, using the one or more computing devices, at least one of a radiation source, or the first adjustable collimator so that the radiation source aligns with a first radiation beam path according to the radiation treatment plan, the attenuation profile of the first adjustable collimator having been adjusted according to the first radiation beam path;
causing, using the one or more computing devices, the radiation source to emit a first radiation beam along the first radiation beam path and through the first adjustable collimator so that the first radiation beam is attenuated according to the attenuation profile of the first adjustable collimator before being delivered to a tumor of the patient;
moving, using the one or more computing devices, at least one of the radiation source, or the second adjustable collimator so that the radiation source aligns with a second radiation beam path according to the radiation treatment plan, the attenuation profile of the second adjustable collimator having been adjusted according to the second radiation beam path; and
causing, using the one or more computing devices, the radiation source to emit a second radiation beam along the second radiation beam path and through the second adjustable collimator so that the second radiation beam is attenuated according to the attenuation profile of the second adjustable collimator before being delivered to the tumor of the patient.

12. The method of claim 11, wherein the first adjustable collimator is moved by at least one of:
rotating, using the one or more computing devices, the first adjustable collimator relative to the radiation source to align the first adjustable collimator with the first radiation beam path; or
translating, using the one or more computing devices, the first adjustable collimator relative to the radiation source to align the first adjustable collimator with the first radiation beam path.

13. The method of claim 11, wherein the radiation treatment plan defines a plurality of radiation beam paths that includes the first radiation beam path, and further comprising:
assigning, using the one or more computing devices, each adjustable collimator to a different radiation beam path of the plurality of radiation beam paths; and
adjusting, using the one or more computing devices, each attenuation profile of each adjustable collimator based on its corresponding radiation beam path.

14. The method of claim 13, wherein each attenuation profile of each adjustable collimator corresponds to a shape of a tumor that is defined by the corresponding radiation beam path, and
wherein each corresponding radiation beam path follows a path that extends from the radiation source and to the patient.

15. The method of claim 13, further comprising:
after emitting the first radiation beam for a period of time, stopping, using the one of the computing devices, the radiation source from emitting the first radiation beam; and
when the radiation source has stopped emitting the first radiation beam, moving, using the one or more computing devices, the at least one of the radiation source, or the first adjustable collimator out of alignment with the first radiation beam path.

16. The method of claim 15, wherein the first adjustable collimator and the second adjustable collimator are multi-leaf collimators (MLCs),
wherein at least one of a size or a shape of a void of the first adjustable collimator at least partially defines its attenuation profile, and
wherein at least one of a size or a shape of a void of the second adjustable collimator at least partially defines its attenuation profile.

17. The method of claim 11, wherein the first radiation beam is emitted for a duration, the duration being between 0.01 seconds and 0.5 seconds, and
wherein the first radiation beam is an X-ray beam.

18. A radiation therapy system, the system comprising:
a radiation therapy source;
a gantry configured to receive a patient bed to arrange the gantry between the radiation therapy source and the patient bed;
a plurality of multi-leaf collimators (MLCs) positioned about the gantry, between the radiation therapy source and the patient bed, the plurality of MLCs including a first MLC and a second MLC; and
a controller configured to:
adjust a configuration of the first MLC to have a first attenuation profile;
adjust a configuration of the second MLC to have a second attenuation profile;
move the first MLC into alignment with the radiation therapy source
cause the radiation therapy source to emit a first radiation therapy beam through the first MLC to attenuate the first radiation therapy beam according to the first attenuation profile;

move the second MLC into alignment with the radiation therapy source; and cause the radiation therapy source to emit a second radiation therapy beam through the second MLC to attenuate the second radiation therapy beam according to the second attenuation profile.

19. The system of claim 18, wherein the plurality of MLCs are arranged about the gantry to form a ring between the patient bed and the radiation therapy source.

20. The system of claim 18, wherein the controller is configured to change an orientation of each of the plurality of MLCs when the radiation therapy source is not arranged to deliver the radiation therapy beam along the beam path associated with a given MLC in the plurality of MLCs.

* * * * *